United States Patent [19]

Robertson et al.

[11] Patent Number: 5,399,574
[45] Date of Patent: Mar. 21, 1995

[54] INDOLYL TETRAHYDROPYRIDINES FOR TREATING MIGRAINE

[75] Inventors: Alan D. Robertson; Alan P. Hill; Robert C. Glen; Graeme R. Martin, all of Beckenham, England

[73] Assignee: Burroughs Wellcome Co., Research Triangle Park, N.C.

[21] Appl. No.: 838,233

[22] PCT Filed: Jun. 6, 1991

[86] PCT No.: PCT/GB91/00908
  § 371 Date: Mar. 3, 1992
  § 102(e) Date: Mar. 3, 1992

[87] PCT Pub. No.: WO91/18897
  PCT Pub. Date: Dec. 12, 1991

[30] Foreign Application Priority Data

Jun. 7, 1990 [GB] United Kingdom ............... 9012672
  Feb. 1, 1991 [GB] United Kingdom ............... 9102182

[51] Int. Cl.$^6$ ............... A61K 31/415; C07D 401/14; C07D 403/14
[52] U.S. Cl. ............... 514/339; 514/323; 514/376; 514/414; 514/415; 546/201; 546/273; 548/229; 548/490; 548/491; 548/504; 548/505; 548/517; 548/518
[58] Field of Search ............... 546/201, 273; 548/229, 548/504, 505, 517, 518, 490, 491; 514/376, 414, 415, 323, 339

[56] References Cited

U.S. PATENT DOCUMENTS

| | | | |
|---|---|---|---|
| 3,320,282 | 5/1967 | von Wittenau et al. | 548/229 |
| 3,873,559 | 3/1975 | Narayanan et al. | 548/518 |
| 3,879,410 | 4/1975 | Bottari et al. | 548/229 |
| 3,931,229 | 1/1976 | Zinnes et al. | 548/504 |
| 3,953,442 | 4/1976 | Demarne | 548/504 |
| 4,042,595 | 8/1977 | Koch et al. | 544/97 |
| 4,049,816 | 9/1977 | Harnden et al. | 548/233 |

(List continued on next page.)

FOREIGN PATENT DOCUMENTS

| | | |
|---|---|---|
| 38298 | 10/1981 | European Pat. Off. . |
| 135863 | 9/1983 | European Pat. Off. . |
| 135348 | 3/1985 | European Pat. Off. . |
| 201735 | 11/1986 | European Pat. Off. . |
| 350437 | 7/1988 | European Pat. Off. . |

(List continued on next page.)

OTHER PUBLICATIONS

Nowakowski, "Preparation of aminoalkylindolylthiazoles as 5HT, receptor agonists" CA 117:251348y (1993).

Clark et al., "Principle of Psychopharmacology", Academic Press, pp. 166–167 (1970).

Glennon, "Central Serotomin Reciptors as targets for dry research", J. Med. Chem. 30, 1–12 (1987).

*Primary Examiner*—Celia Chang
*Attorney, Agent, or Firm*—Nixon & Vanderhye

[57] ABSTRACT

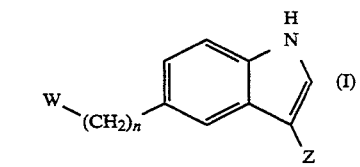

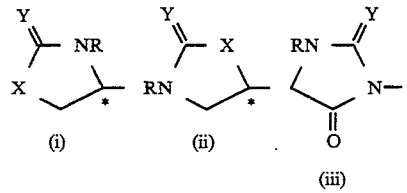

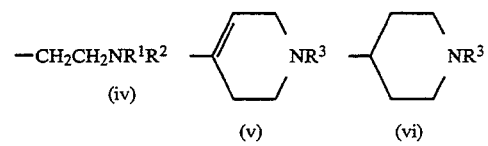

The present invention is concerned with compounds of formula (I), wherein n is an integer of from 0 to 3: W is a group of formula (i), (ii), or (iii), wherein R is hydrogen or C$_{1-4}$ alkyl, X is —O—, —S—, —NH—, or —CH$_2$—, Y is oxygen or sulphur and the chiral center (*) in formula (i) or (ii) is in its (S) or (R) form or is a mixture thereof in any proportions: and Z is a group of formula (iv), (v), or (vi), wherein R$^1$ and R$^2$ are independently selected from hydrogen and C$_{1-4}$ alkyl and R$^3$ is hydrogen or C$_{1-4}$ alkyl; and their salts, solvates and physiologically functional derivatives, with processes for their preparation, with medicaments containing them and with their use as therapeutic agents, particularly in the prophylaxis and treatment of migraine.

5 Claims, No Drawings

U.S. PATENT DOCUMENTS

| Number | Date | Inventor | Class |
|---|---|---|---|
| 4,062,862 | 12/1977 | Fujimoto et al. | 548/229 |
| 4,137,404 | 1/1979 | Batcho et al. | 548/228 |
| 4,148,895 | 4/1979 | Lattrell et al. | 546/201 |
| 4,188,323 | 2/1980 | Pestellini et al. | 548/229 |
| 4,198,501 | 4/1980 | Batcho et al. | 542/443 |
| 4,236,012 | 11/1980 | Fujimoto et al. | 548/229 |
| 4,252,803 | 2/1981 | Webb | 544/373 |
| 4,255,432 | 3/1981 | Kluge et al. | 546/19 |
| 4,272,555 | 6/1981 | Davis et al. | 252/373 |
| 4,287,351 | 9/1981 | Bourgery et al. | 548/232 |
| 4,348,393 | 9/1982 | Bourgery et al. | 548/232 |
| 4,367,234 | 1/1983 | Schnur | 548/226 |
| 4,399,296 | 8/1983 | Schnur | 556/416 |
| 4,407,811 | 10/1983 | Schnur | 424/272 |
| 4,413,001 | 11/1983 | Bourgery et al. | 424/272 |
| 4,435,415 | 3/1984 | Bougery et al. | 548/229 |
| 4,448,971 | 5/1984 | Schnur | 548/226 |
| 4,500,717 | 2/1985 | Cook et al. | 548/229 |
| 4,526,786 | 7/1985 | Bourgery et al. | 514/240 |
| 4,636,521 | 1/1987 | Coates et al. | 514/415 |
| 4,650,810 | 3/1987 | Bays et al. | 514/415 |
| 4,672,067 | 6/1987 | Coates et al. | 548/504 |
| 4,753,956 | 6/1988 | Schnur | 514/365 |
| 4,774,240 | 9/1988 | Boshagen et al. | 548/504 |
| 4,785,016 | 11/1988 | Evans et al. | 514/415 |
| 4,795,756 | 1/1989 | Oxford et al. | 514/415 |
| 4,801,600 | 1/1989 | Wang et al. | 548/229 |
| 4,803,218 | 2/1989 | Stanley et al. | 514/414 |
| 4,816,470 | 3/1989 | Dowle et al. | 514/415 |
| 4,831,153 | 5/1989 | Van Phung | 548/231 |
| 4,833,153 | 5/1989 | Dowle et al. | 514/415 |
| 4,839,377 | 6/1989 | Bays et al. | 514/415 |
| 4,851,406 | 7/1989 | Mertens et al. | 514/212 |
| 4,855,314 | 8/1989 | Oxford et al. | 514/415 |
| 4,870,085 | 9/1989 | Glaser et al. | 514/323 |
| 4,870,086 | 9/1989 | Sandberg | 514/330 |
| 4,921,869 | 5/1990 | Wang et al. | 548/229 |
| 4,965,268 | 10/1990 | Wang | 568/229 |
| 4,980,368 | 12/1990 | Thielke et al. | 514/415 |
| 4,994,483 | 2/1991 | Oxford et al. | 514/415 |
| 4,997,841 | 3/1991 | Oxford et al. | 514/323 |
| 5,036,078 | 6/1991 | Coates | 514/323 |
| 5,164,510 | 11/1992 | Brickner | 548/231 |

FOREIGN PATENT DOCUMENTS

| Number | Date | Country |
|---|---|---|
| 0303506 | 2/1989 | European Pat. Off. |
| 308744 | 3/1989 | European Pat. Off. |
| 359418 | 3/1989 | European Pat. Off. |
| 311090 | 4/1989 | European Pat. Off. |
| 0313397 | 4/1989 | European Pat. Off. |
| 0354777 | 2/1990 | European Pat. Off. |
| 501568 | 2/1992 | European Pat. Off. |
| 2611089 | 10/1976 | Germany |
| 3643957 | 12/1986 | Germany |
| 3939238 | 11/1989 | Germany |
| 57-04986 | 1/1982 | Japan |
| 57-169458 | 10/1982 | Japan |
| 1386613 | 2/1972 | United Kingdom |
| 1382943 | 2/1973 | United Kingdom |
| 1398687 | 4/1973 | United Kingdom |
| 1467404 | 3/1974 | United Kingdom |
| 1471007 | 7/1974 | United Kingdom |
| 1482879 | 7/1975 | United Kingdom |
| 1469200 | 11/1975 | United Kingdom |
| 1573809 | 12/1976 | United Kingdom |
| 2032423 | 5/1980 | United Kingdom |
| 2119372 | 11/1983 | United Kingdom |
| 2168347 | 6/1986 | United Kingdom |
| 2186874 | 8/1987 | United Kingdom |
| WO90/02744 | 3/1990 | WIPO |
| WO91/16304 | 10/1991 | WIPO |

INDOLYL TETRAHYDROPYRIDINES FOR TREATING MIGRAINE

The present invention is concerned with new chemical compounds, their preparation, pharmaceutical formulations containing them and their use in medicine, particularly the prophylaxis and treatment of migraine.

Receptors which mediate the actions of 5-hydroxytryptamine (5-HT) have been identified in mammals in both the periphery and the brain. According to the classification and nomenclature proposed in a recent article (Bradley et al, Neuropharmac., 25, 563 (1986)), these receptors may be classified into three main types, viz. "5-$HT_1$-like", 5-$HT_2$ and 5-$HT_3$. Various classes of compounds have been proposed as 5-HT agonists or antagonists for therapeutic use, but these have not always been specific to a particular type of 5-HT receptor. European Patent Specification 0313397 describes a class of 5-HT agonists which are specific to a particular type of "5-$HT_1$-like" receptor and are effective therapeutic agents for the treatment of clinical conditions in which a selective agonist for this type of receptor is indicated. For example, the receptor in question mediates vasoconstriction in the carotid vascular bed and thereby modifies blood flow therein. The compounds described in the European specification are therefore beneficial in the treatment or prophylaxis of conditions wherein vasoconstriction in the carotid vascular bed is indicated, for example, migraine, a condition associated with excessive dilation of the carotid vasculature. However, it is within the scope of the earlier application that the target tissue may be any tissue wherein action is mediated by "5-$HT_1$-like" receptors of the type referred to above.

We have now found a further class of compounds having exceptional "5-$HT_1$-like" receptor agonism and excellent absorption following oral dosing. These properties render the compounds particularly useful for certain medical applications, notably the prophylaxis and treatment of migraine, cluster headache and headache associated with vascular disorders, hereinafter referred to collectively as "migraine".

According to the first aspect of the present invention, therefore, there is provided a compound of formula (I)

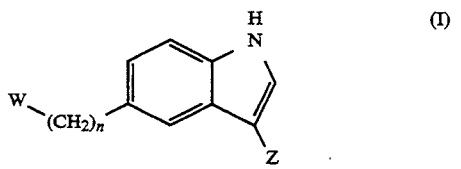

wherein
n is an integer of from 0 to 3;
W is a group of formula (i), (ii), or (iii)

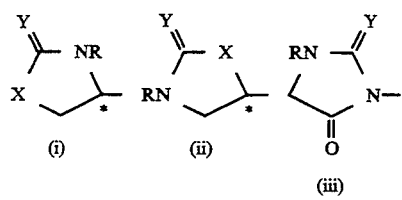

wherein R is hydrogen or $C_{1-4}$ alkyl, X is —O—, —S—, —NH—, or —$CH_2$—, Y is oxygen or sulphur and the chiral centre * in formula (i) or (ii) is in its (S) or (R) form or is a mixture thereof in any proportions; and
Z is a group of formula (iv), (v), or (vi)

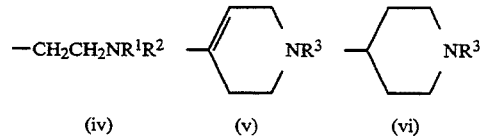

wherein $R^1$ and $R^2$ are independently selected from hydrogen and $C_{1-4}$ alkyl and $R^3$ is hydrogen or $C_{1-4}$ alkyl;
and salts, solvates and physiologically functional derivatives thereof.

Compounds of formula (I) having particularly desirable properties for the treatment and prophylaxis of migraine include those wherein n is 1, W is a group of formula (i) and Z is a group of formula (iv) or (vi). Of these, compounds of formula (I) wherein n is 1, W is a group of formula (i) wherein R is hydrogen, X is —O— and Y is oxygen and Z is a group of formula (iv) or (vi) wherein $R^1 = R^2 =$ hydrogen or methyl are particularly preferred.

Two compounds of formula (I) having exceptional properties for the treatment and prophylaxis of migraine are N,N-dimethyl-2-[5-(2-oxo-1,3-oxazolidin-4-yl-methyl)-1H-indol-3-yl]ethylamine and 3-(1-methyl-4-piperidyl)-5-(2-oxo-1,3-oxazolidin-4-ylmethyl)-1H-indole in either their (S) or (R) form or as a mixture thereof in any proportions. The salts and solvates of these compounds, for example, the hydrate maleates, are particularly preferred.

Physiologically acceptable salts are particularly suitable for medical applications because of their greater aqueous solubility relative to the parent, i.e. basic, compounds. Such salts must clearly have a physiologically acceptable anion. Suitable physiologically acceptable salts of the compounds of the present invention include those derived from acetic, hydrochloric, hydrobromic, phosphoric, malic, maleic, fumaric, citric, sulphuric, lactic, or tartaric acid. The succinate and chloride salts are particularly preferred for medical purposes. Salts having a non-physiologically acceptable anion are within the scope of the invention as useful intermediates for the preparation of physiologically acceptable salts and/or for use in non-therapeutic, for example, in vitro, situations.

According to a second aspect of the present invention, there is provided a compound of formula (I) or a physiologically acceptable salt, solvate, or physiologically functional derivative thereof for use as a therapeutic agent, specifically as a "5-$HT_1$-like" receptor agonist, for example, as a carotid vasoconstrictor in the prophylaxis and treatment of migraine. As indicated, however, target organs for the present compounds other than the carotid vasculature are within the scope of the present invention.

The amount of a compound of formula (I), or a salt or solvate thereof, which is required to achieve the desired biological effect will depend on a number of factors such as the specific compound, the use for which it is intended, the means of administration, and the recipient. A typical daily dose for the treatment of migraine may be expected to lie in the range 0.01 to 5 mg per kilogram body weight. Unit doses may contain from 1 to 100 mg of a compound of formula (I), for example, ampoules for injection may contain from 1 to 10 mg and orally administrable unit dose formulations such as tablets or capsules may contain from 1 to 100 mg. Such unit doses may be administered one or more times a day, separately or in multiples thereof. An intravenous dose may be expected to lie in the range 0.01 to 0.15 mg/kg and would typically be administered as an infusion of from 0.0003 to 0.15 mg per kilogram per minute. Infusion solutions suitable for this purpose may contain from 0.01 to 10 mg/ml.

When the active compound is a salt or solvate of a compound of formula (I), the dose is based on the cation (for salts) or the unsolvated compound.

Hereinafter references to "compound(s) of formula (I)" will be understood to include physiologically acceptable salts and solvates thereof.

According to a third aspect of the present invention, therefore, there are provided pharmaceutical compositions comprising, as active ingredient, at least one compound of formula (I) and/or a pharmacologically acceptable salt or solvate thereof together with at least one pharmaceutical carrier or excipient. These pharmaceutical compositions may be used in the prophylaxis or treatment of clinical conditions for which a "5-HT$_1$-like" receptor agonist is indicated, for example, migraine. The carrier must be pharmaceutically acceptable to the recipient and must be compatible with, i.e. not have a deleterious effect upon, the other ingredients in the composition. The carrier may be a solid or liquid and is preferably formulated with at least one compound of formula (I) as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example, subcutaneous, intramuscular, or intravenous), rectal, topical and intranasal administration. The most suitable means of administration for a particular patient will depend on the nature and severity of the condition being treated and on the nature of the active compound, but, where possible, oral administration is preferred.

Formulations suitable for oral administration may be provided as discrete units, such as tablets, capsules, cachets, or lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically, a flavoured base, such as sugar and acacia or tragacanth, and pastilles comprising the active compound in an inert base, such as gelatin and glycerin or sucrose and acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient and one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethylene glycols, alcohols, and combinations thereof. The active ingredient is typically present in such formulations at a concentration of from 0.1 to 15% w/w.

The formulations of the invention may be prepared by any suitable method, typically by uniformly and intimately admixing the active compound(s) with liquids or finely divided solid carriers, or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions for parenteral administration are typically prepared by dissolving the active compound in sufficient water to give the desired concentration and then rendering the resulting solution sterile and isotonic.

Thus, according to a fourth aspect of the present invention, there is provided the use of a compound of formula (I) in the preparation of a medicament for the prophylaxis or treatment of a clinical condition for which a "5-HT$_1$-like" receptor agonist is indicated, for example, migraine.

According to a fifth aspect, there is provided a method for the prophylaxis or treatment of a clinical condition in a mammal, for example, a human, for which a "5-HT$_1$-like" receptor agonist is indicated, for example, migraine, which comprises the administration to said mammal of a therapeutically effective amount of a compound of formula (I) or of a physiologically acceptable salt, solvate, or physiologically functional derivative thereof.

According to a sixth aspect of the invention, compounds of formula (I) wherein Z is a group of formula (iv) may be prepared by reacting a compound of formula (II) (isolated or in situ-infra).

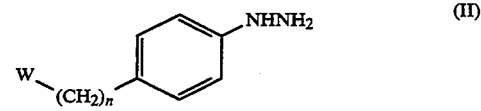

wherein n and W are as hereinbefore defined with a compound of formula (III)

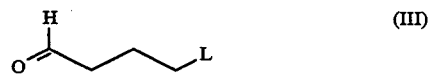

or a carbonyl-protected form thereof, such as the dimethyl or diethyl acetal, wherein L is a suitable leaving group, such as chlorine, or a protected amino group, either of which may be converted in situ to an amino group, or is —NR$^1$R$^2$ where R$^1$ and R$^2$ are as hereinbefore defined. The reaction is typically carried out by refluxing the compounds in a polar solvent system, for example, ethanol/water, dilute acetic acid, or water in the presence of an acidic ion exchange resin, for example. 'Amberlyst 15'.

Standard N-alkylation methods may be used to convert compounds of formula (I) wherein Z is a group of formula (iv) and $R^1$ and/or $R^2$ are hydrogen to corresponding compounds wherein $R^1$ and/or $R^2$ are $C_{1-4}$ alkyl.

Compounds of formula (I) wherein Z=(iv) and $R^1=R^2=C_{1-4}$ alkyl may be prepared from the corresponding compound wherein $R^1=R^2=H$ by methods of N,N-dialkylation well known to those skilled in the art, for example, by treatment with the appropriate aldehyde in the presence of a reducing system, for example, sodium cyanoborohydride/acetic acid, in a polar solvent, such as methanol.

Compounds of formula (I) wherein Z=(iv) and $R^1$ or $R^2=C_{1-4}$ alkyl may be prepared from the corresponding compound wherein $R^1=R^2=H$ by N-benzylation using benzaldehyde and a suitable reducing agent, for example, sodium borohydride, in a polar solvent, such as ethanol, followed by N-alkylation using a suitable agent, such as the appropriate dialkyl sulphate, typically in the presence of a base, for example, anhy. potassium carbonate, in a polar aprotic solvent, such as DMF, and finally N-debenzylation, typically by catalytic hydrogenation using, for example, Pd/C in a polar solvent, such as ethanol.

Hydrazines of formula (II) may be prepared from the corresponding aniline of formula (IV)

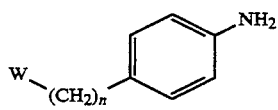
(IV)

wherein n and W are as hereinbefore defined, by diazotisation followed by reduction. Diazotisation is typically carried out using sodium nitrite/c.HCl and the resulting diazo product reduced in situ using, for example, tin(II) chloride/c.HCl. The resulting hydrazine may be isolated or converted to a compound of formula (I) in situ.

Anilines of formula (IV) may be prepared by reduction of the corresponding p-nitro compound of formula (V)

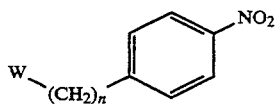
(V)

wherein n and W are as hereinbefore defined, typically by catalytic hydrogenation using, for example, Pd/C in a polar solvent system, such as an acidified mixture of ethanol, water and ethyl acetate.

Anilines of formula (IV) wherein W is a group of formula (i) or (ii) may also be prepared by cyclising a compound of formula (XXXIII)

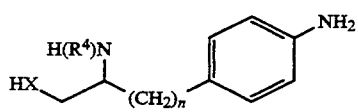
(XXXIII)

or

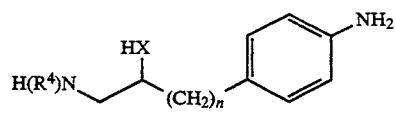
(XXXIV)

wherein n and X are as hereinbefore defined and $R^4$ is $-CO_2R^5$ where $R^5$ is $C_{1-4}$ alkyl, typically by heating in the presence of a base, such as sodium methoxide.

Compounds of formula (XXXIII) wherein X is oxygen may be prepared by reducing a corresponding $C_{1-4}$ alkyl ester using, for example, sodium borohydride, in a polar solvent system, such as ethanol/water, at 0° C. The ester may be prepared by esterifying the corresponding carboxylic acid using, for example, the appropriate alcohol and HCl or by reducing the corresponding p-nitro compound, for example, by catalytic hydrogenation. Both the acid and the p-nitro compound may be prepared from the corresponding p-nitroaminoacid, the acid by N-alkoxycarbonylation using, for example, $R^5OCOCl$ where $R^5$ is as hereinbefore defined, followed by reduction of the nitro group, for example, by catalytic hydrogenation, or by reduction of the nitro group followed by N-alkoxycarbonylation, and the p-nitro compound by N-alkoxycarbonylation (as for the acid) followed by esterification using, for example, the appropriate alcohol and HCl, or by esterification followed by N-alkoxycarbonylation. The p-nitroaminoacid may be obtained commercially or prepared from readily available starting materials by methods known to those skilled in the art or obtainable from the chemical literature, for example, by p-nitration of the corresponding aminoacid using, for example, c.$H_2SO_4$/c.$HNO_3$ at 0° C.

Compounds of formula (XXXIV) wherein X is oxygen may be prepared by reducing the corresponding dinitro compound, typically by catalytic hydrogenation using, for example, Pd/C in a polar solvent, such as ethanol. The dinitro compound may be prepared by reacting the appropriate aldehyde with nitromethane, typically in the presence of a base, for example, sodium methoxide, in a polar solvent, such as methanol, followed by p-nitration using, for example, c.$H_2SO_4$/c.$HNO_3$, or by p-nitration of the appropriate aldehyde followed by reaction with nitromethane. The aldehyde may be obtained commercially or prepared from readily available starting materials by methods known to those skilled in the art or obtainable from the chemical literature.

p-Nitro compounds of formula (V) may be prepared by
(a) in the case where W is a group of formula (i) in which Y is oxygen or sulphur, reacting a compound of formula (VI)

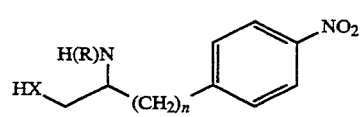
(VI)

wherein n, R and X are as hereinbefore defined, with a compound of formula (VII)

wherein Y is as hereinbefore defined and L and L', which may be the same or different, are suitable leaving groups, for example, chlorine, ethoxy, trichloromethyl, trichloromethoxy, or imidazoyl, for example, in the case where L-L'-chlorine, in a non-polar solvent, such as toluene, in the presence of a base, for example, potassium hydroxide.

(b) in the case where W is a group of formula (ii) in which Y is oxygen or sulphur, reacting a compound of formula (VIII)

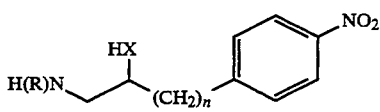

wherein n, R and X are as hereinbefore defined, with a compound of formula (VII) wherein Y, L and L' are as hereinbefore defined, typically using the reaction conditions described in (a);

(c) in the case where W is a group of formula (iii), reacting a compound of formula (IX)

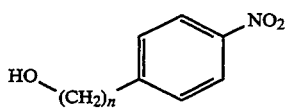

wherein n is as hereinbefore defined, with a compound of formula (X)

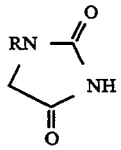

wherein R is as hereinbefore defined, typically in a polar aprotic solvent, such as DMF, in the presence of DEAD/Ph$_3$P.

Compounds of formula (VI) may be prepared by ring-opening a compound of formula (V) wherein n is as hereinbefore defined and W is a group of formula (i) in which R, X and Y are as hereinbefore defined, for example, by refluxing in 2N aqu. KOH.

Compounds of formula (VI) wherein X is oxygen may be prepared by esterification of the corresponding carboxylic acid, typically by treatment with thionyl chloride and an appropriate alcohol at −10° C. followed by reduction of the ester using, for example, sodium borohydride, in a polar solvent system, such as ethanol/water, at 0° C. The acid may be obtained commercially or prepared from readily available starting materials by methods known to those skilled in the art or obtainable from the chemical literature, for example, by p-nitration of the corresponding aminoacid using, for example, c.H$_2$SO$_4$/c.HNO$_3$ at 0° C.

Compounds of formula (VIII) may be prepared by ring-opening a compound of formula (V) wherein n is a hereinbefore defined and W is a group of formula (ii) in which R, X and Y are as hereinbefore defined, for example, by refluxing in 2N aqu. KOH.

Compounds of formula (III), (VII), (IX) and (X) may be obtained commercially or prepared from readily available starting materials by methods known to those skilled in the art or obtainable from the chemical literature.

p-Nitro compounds of formula (V) wherein W is a group of formula (i) or (ii) may also be prepared by p-nitration of a compound of formula (XXXVI)

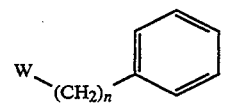

wherein n and W are as hereinbefore defined, using, for example, c.H$_2$SO$_4$/c.HNO$_3$ at 0° C.

Compounds of formula (XXXVI) may be prepared by reacting a compound of formula (XXXVII)

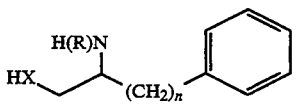

or

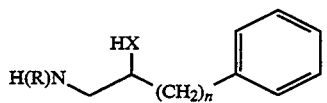

wherein n, R and X are as hereinbefore defined, with a compound of formula (VII) wherein Y, L and L' are as hereinbefore defined, typically in the presence of a base, for example, potassium hydroxide, in a non-polar solvent, such as toluene.

Compounds of formula (XXXVII) and (XXXVIII) may be prepared by reducing the corresponding nitro compounds, typically by catalytic hydrogenation using, for example, Pd/C in a polar solvent, such as ethanol. The nitro compound corresponding to the compound of formula (XXXVII) may be prepared by reacting a compound of formula (XXIV)

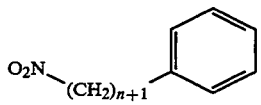

wherein n is a hereinbefore defined, with paraformaldehyde in a polar aprotic solvent, such as DMF, in the presence of a base, for example, sodium methoxide, at 0° C., or by esterification of the corresponding carboxylic acid, typically by treatment with thionyl chloride and an appropriate alcohol at −10° C., followed by reduction of the ester group using, for example, sodium borohydride, in a polar solvent system, such as ethanol/water, at 0° C. The nitro compound corresponding to the compound of formula (XXXVIII) may be prepared by reacting the appropriate aldehyde with nitromethane, typically in the presence of a base, for example, sodium methoxide, in a polar solvent, such as methanol. The compound of formula (XXIV), the acid and the aldehyde may be obtained commercially or prepared from readily available starting materials by methods known to those skilled in the art or obtainable from the chemical literature.

p-Nitro compounds of formula (V) wherein W is a group of formula (i), (ii), or (iii) in which R is $C_{1-4}$ alkyl may be prepared from the corresponding compound of formula (V) wherein R is hydrogen by N-alkylation using a suitable agent, such as the appropriate dialkyl sulphate, typically in the presence of a base, for example, sodium hydride, in a non-polar solvent, such as THF.

Compounds of formula (I) wherein W is a group of formula (i) or (ii) may also be prepared by reacting a compound of formula (XV)

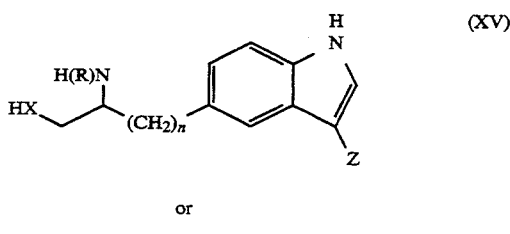

or

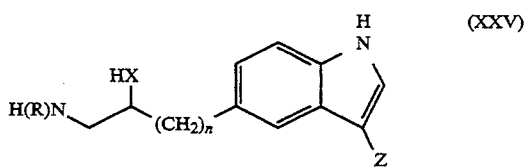

wherein n, R, X and Z are as hereinbefore defined, with a compound of formula (VII) wherein Y, L and L' are as hereinbefore defined, for example, in the case where L-L'-ethoxy, by heating in the presence of a base, for example, potassium carbonate.

Compounds of formula (XV) may be prepared by ring-opening a compound of formula (I) wherein n and Z are as hereinbefore defined and W is a group of formula (i) in which R, X and Y are as hereinbefore defined, for example, by refluxing in 2N aqu. KOH.

Compounds of formula (XV) wherein X is oxygen may be prepared by esterification of the corresponding carboxylic acid, typically by treatment with thionyl chloride and an appropriate alcohol at $-10°$ C., followed by reduction of the ester using, for example, sodium borohydride, in a polar solvent system, such as ethanol/water, at $0°$ C. The acid may be prepared by ring-opening a compound of formula (XVI)

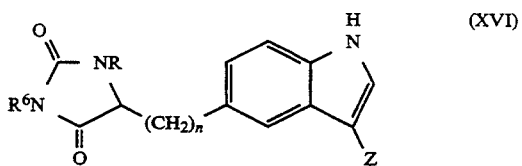

wherein n, R and Z are as hereinbefore defined and $R^6$ is hydrogen or benzyl, typically by refluxing in water in the presence of a base, for example, barium hydroxide.

Compounds of formula (XVI) wherein $n \neq 0$ may be prepared by reducing a compound of formula (XVII)

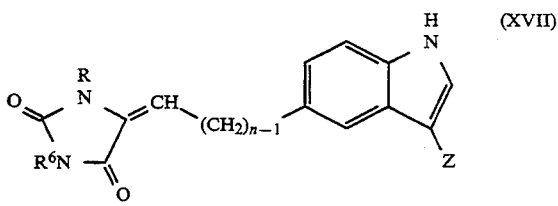

wherein n, R, $R^6$ and Z are as hereinbefore defined, typically by catalytic hydrogenation using, for example, Pd/C in a polar solvent system, such as ethanol/water. Alternatively, an enantioselective reducing agent, such as Rh(cod) (dipamp) $BF_4^-$(JCS. Chem. Comm. 275 (1991)), may be used to reduce the double bond and thereby introduce a chiral centre at the 4-position of the dioxoimiazole ring. The reduction step may be used to convert a compound of formula (XVII) wherein Z is a group of formula (v) into a compound of formula (XVI) wherein Z is a group of formula (vi).

Compounds of formula (XVII) may be prepared by reacting a compound of formula (XVIII)

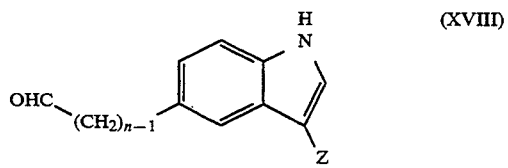

wherein n and Z are as hereinbefore defined, with, in the case where $R^6$ is to be hydrogen, a compound of formula (X) wherein R is as hereinbefore defined, typically by heating in glac. acetic acid in the presence of ammonium acetate.

Compounds of formula (XVIII) may be prepared by the reduction hydrolysis of the corresponding nitrile, typically using Raney nickel and sodium hypophosphite in a mixture of water, acetic acid and pyridine. The nitrile may be prepared by reacting a compound of formula (XIX)

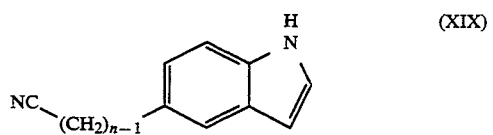

wherein n is as hereinbefore defined, with, in the case where Z is to be a group of formula (v) or (vi), the appropriate compound of formula (XXVIII)

wherein $R^3$ is as hereinbefore defined, typically by refluxing in a polar solvent, such as methanol, in the presence of base, for example, potassium hydroxide.

Compounds of formula (XIX) and (XXVIII) may be obtained commercially or prepared from readily available starting materials by methods known to those skilled in the art or obtainable from the chemical literature. Compounds of formula (XVI) wherein n=0 may be obtained by the same means.

Compounds of formula (XVI) wherein $R^6$ is benzyl and Z is a group of formula (iv) may be prepared by reacting a compound of formula (XXXV)

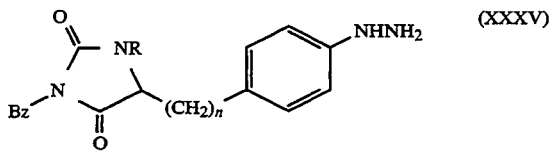
(XXXV)

wherein n and R are as hereinbefore defined, with a compound of formula (III) wherein L is as hereinbefore defined, typically using the reaction conditions described above for the reaction of (II) with (III).

Hydrazines of formula (XXXV) may be prepared from the corresponding aniline, typically using the reaction conditions described above for the conversion of (IV) to (II). The aniline may be prepared by reducing the corresponding p-nitro compound, typically using the reaction conditions described above for the conversion of (V) to (IV). The p-nitro compound may be prepared by reacting the corresponding p-nitroaminoacid with benzyl isocyanate in the presence of base, for example, potassium hydroxide, in a polar solvent, such as water. The p-nitroaminoacid may be obtained commercially or prepared from readily available starting materials by methods known to those skilled in the art or obtainable from the chemical literature, for example, by p-nitration of the corresponding aminoacid using, for example, c.$H_2SO_4$/c.$HNO_3$ at 0° C.

Compounds of formula (XV) wherein R is hydrogen may be prepared by reducing a compound of formula (XX)

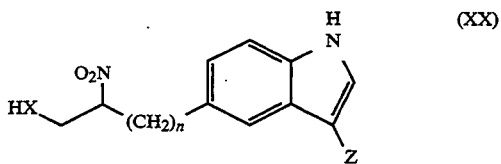
(XX)

wherein n, X and Z are as hereinbefore defined, typically by catalytic hydrogenation using, for example Pd/C in a polar solvent, such as ethanol. The same step may be used to convert a compound of formula (XX) wherein Z is a group of formula (v) into a compound of formula (XV) wherein Z is a group of formula (vi).

Compounds of formula (XX) wherein X is oxygen may be prepared by reacting a compound of (XXI)

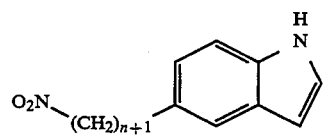
(XXI)

wherein n and Z are as hereinbefore defined, with paraformaldehyde in a polar aprotic solvent, such as DMF, in the presence of a base, for example, sodium methoxide, at 0° C.

Compounds of formula (XXI) may be prepared by reacting a compound of formula (XXII)

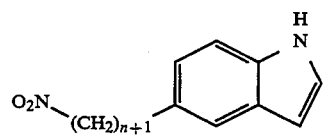
(XXII)

wherein n is as hereinbefore defined, with, in the case where Z is to be a group of formula (v) or (vi), the appropriate compound of formula (XXVIII) wherein $R^3$ is as hereinbefore defined, typically by heating in glac. acetic acid.

Compounds of formula (XXII) wherein $n \neq 0$ may be prepared by reducing a compound of formula (XXIII)

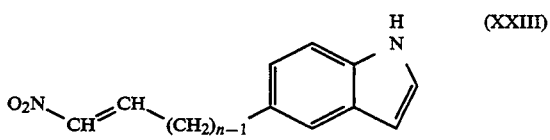
(XXIII)

wherein n is as hereinbefore defined, using, for example, sodium borohydride and 40% w/v aqu. NaOH in a polar aprotic solvent, such as acetonitrile, at 0° C.

Compounds of formula (XXIII) may be prepared by heating the appropriate aldehyde with nitromethane in the presence of ammonium acetate. The aldehyde may be prepared from a compound of formula (XIX) wherein n is as hereinbefore defined using the reaction conditions described above for preparing a compound of formula (XVIII) from the corresponding nitrile.

Compounds of formula (XXII) wherein n=0 may be obtained commercially or prepared from readily available starting materials by methods known to those skilled in the art or obtainable from the chemical literature.

Compounds of formula (XXI) wherein $n \neq 0$ may also be prepared from a compound of formula (XXXIX)

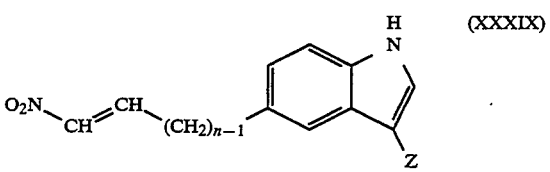
(XXXIX)

wherein n and Z are as hereinbefore defined, using reaction conditions analogous to those used to convert (XXIII) to (XXII). Compounds of formula (XXXIX) may be prepared from a compound of formula (XVIII) wherein n and Z are as hereinbefore defined using reaction conditions analogous to those used to prepare (XXIII) from the appropriate aldehyde and nitromethane.

Compounds of formula (XX) wherein X is other than oxygen may be obtained commercially or prepared from readily available starting materials by methods known to those skilled in the art or obtainable from the chemical literature.

Compounds of formula (XXV) may be prepared by ring-opening a compound of formula (I) wherein n and Z are as hereinbefore defined and W is a group of formula (ii) in which R, X and Y are as hereinbefore defined, for example, by refluxing in 2N aqu. KOH.

Compounds of formula (I) wherein W is a group of formula (i) in which Y is sulphur may be prepared by refluxing a compound of formula (XV) wherein n, R and X are as hereinbefore defined, with a compound of formula (VII) wherein Y is sulphur and L and L' are as hereinbefore defined, for example, N,N'-thiocarbonylimidazole, typically in an aprotic solvent, such as THF.

Compounds of formula (I) wherein W is a group of formula (ii) in which Y is sulphur may be prepared by refluxing a compound of formula (XXV) wherein n, R and X are as hereinbefore defined, with a compound of formula (VII) wherein Y is sulphur and L and L' are as hereinbefore defined, for example, N,N'-thiocarbonylimidazole, typically in an aprotic solvent, such as THF.

Compounds of formula (I) wherein W is a group of formula (iii) and Z is a group of formula (v) or (vi) may also be prepared by cyclising a compound of formula (XXVI)

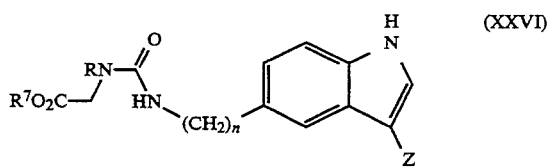

wherein n and R are as hereinbefore defined, Z is a group of formula (v) or (vi) and $R^7$ is $C_{1-4}$ alkyl, typically by heating in aqueous acid, for example, 2N HCl.

Compounds of formula (XXVI) wherein Z is a group of formula (v) may be prepared by reacting a compound of formula (XXVII)

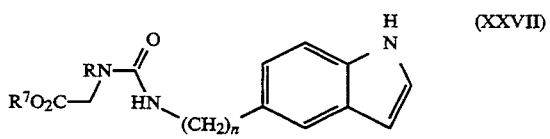

wherein n, R and $R^7$ are as hereinbefore defined, with a compound of formula (XXVIII) wherein $R^3$ is as hereinbefore defined, typically by heating in a non-aqueous acid, for example, glac. acetic acid.

Compounds of formula (XXVI) wherein Z is a group of formula (vi) may be prepared by reducing a compound of formula (XXVI) wherein Z is a group of formula (v), typically by catalytic hydrogenation using, for example, Pd/C in a polar solvent system, such as acidified methanol/water.

Compounds of formula (XXVII) may be prepared by reacting a compound of formula (XXIX)

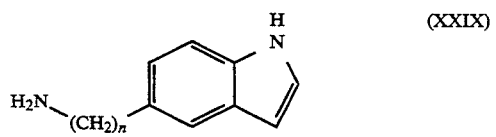

wherein n is as hereinbefore defined, with a compound of formula (XXX)

wherein $R^7$ is as hereinbefore defined, typically in an aprotic solvent, such as DCM.

Compounds of formula (XXIX) and (XXX) may be obtained commercially or prepared from readily available starting materials by methods known to those skilled in the art or obtainable from the chemical literature.

Compounds of formula (I) wherein Z is a group of formula (iv) may also be prepared from a compound of formula (XXXI)

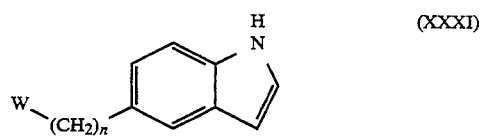

wherein n and W are as hereinbefore defined, by methods known to those skilled in the art or obtainable from the chemical literature, for example, by treatment with $(COL)_2$, where L is a suitable leaving group, for example, chlorine, to give the corresponding 3-COCOL compound which may then be treated with $HNR^1R^2$, where $R^1$ and $R^2$ are as hereinbefore defined, and reduced using, for example, lithium aluminium hydride. Alternatively, the compound of formula (XXXI) may be treated with $CH_2O/KCN$ to give the corresponding 3-cyanomethyl compound which may then be catalytically hydrogenated over Raney nickel in the presence of $HNR^1R^2$ as hereinbefore defined.

The aforementioned 3-cyanomethyl compound may also be prepared by cyclising a compound of formula (XXXX)

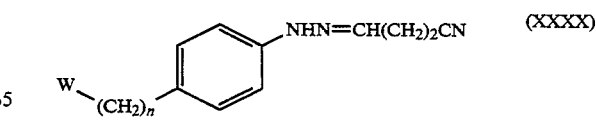

wherein n and W are as hereibefore defined, typically by refluxing in an aprotic solvent, such as chloroform, in the presence of polyphosphate ester.

Compounds of formula (XXXX) may be prepared by reacting a compound of formula (II) wherein n and W are as hereinbefore defined with 3-cyanopropanal, or a carbonyl-protected form thereof, such as the diethyl acetal, typically in an aqueous acid, for example, dil. HCl.

Compounds of formula (I) wherein Z is a group of formula (v) may also be prepared by reacting a compound of formula (XXXI) wherein n and W are as hereinbefore defined, with a compound of formula (XXVIII) wherein $R^3$ is as hereinbefore defined, typically by heating in glac. acetic acid.

Compounds of formula (XXXI) may be prepared by reducing a compound of formula (XXXII)

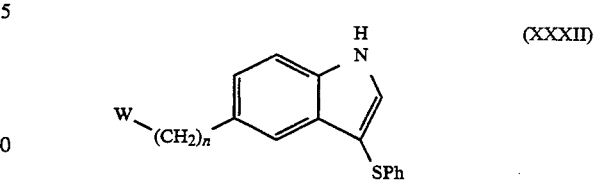

wherein n and W are as hereinbefore defined, typically by heating with Raney nickel in a polar solvent, such as IPA.

Compounds of formula (XXXII) may be prepared by reacting a hydrazine of formula (II) wherein n and W are as hereinbefore defined with phenylthioacetaldehyde, or a carbonyl-protected form thereof, for example, the diethyl acetal, in a polar solvent, such as acidified ethanol.

Compounds of formula (I) wherein Z is group of formula (vi) may also be prepared by reducing a compound of formula (I) wherein Z is a group of formula (v), typically by catalytic hydrogenation using, for example, Pd/C in a polar solvent system, such as acidified methanol/water.

For a better understanding of the invention, the following Examples are given by way of illustration.

SYNTHETIC EXAMPLES

Synthetic Example 1

Preparation of (S)-2-[5-(2-oxo-1,3-oxazolidin-4-ylmethyl)-1H-indol-3-yl]ethylamine (a) (S)-Methyl 4-nitrophenylalanate hydrochloride Methanol (110 ml) was treated dropwise with thionyl chloride (26.3 g) at −10° C. and L-4-nitrophenylalanine (Fluka, 21.7 g) added to the resulting solution as a solid. The mixture was stirred overnight at room temperature and the methanol removed in vacuo to give the desired product as a pale yellow solid (21.2 g).

(b) (S)-2-Amino-3-(4-nitrophenyl)propanol

The product from step (a) (21.2 g) was dissolved in ethanol/water (190 ml, 100/90 v/v) and the solution added dropwise at 0° C. to a stirred solution of sodium borohydride (13.0 g) in ethanol/water (190 ml, 100/90 v/v). The resulting mixture was refluxed for 2.5 hours, cooled and the precipitate filtered off. The ethanol was partially removed from the filtrate in vacuo and the resulting precipitate filtered off and dried to give the desired product as a pale yellow solid (7.5 g).

(c) (S)-4-(4-Nitrobenzyl)-1,3-oxazolidin-2-one

The product from step (b) (4.9 g) was suspended in toluene, the suspension cooled to 0° C. and a solution of potassium hydroxide (7.0 g) in water (56 ml) added dropwise. A solution of phosgene (62.5 ml of a 12% w/v solution in toluene) was added dropwise to the resulting solution over 30 minutes and stirring continued for 1 hour. The mixture was extracted with ethyl acetate and the extracts washed with brine, dried and evaporated in vacuo to give a yellow oil. Crystallisation from ethyl acetate gave the desired product as pale yellow crystals (2.3 g).

(d) (S)-4-(4-Aminobenzyl)-1,3-oxazolidin-2-one hydrochloride

A suspension of the product from step (c) (0.79 g) and 10% palladium on carbon (0.26 g) in a mixture of ethanol (15 ml), water (11 ml), ethyl acetate (2.0 ml) and aqu. 2N HCl (2.3 ml) was stirred under 1 atmos. pressure of hydrogen until uptake ceased. The mixture was filtered through Hyflo and the filtrate evaporated in vacuo to give the desired product as a pale yellow foam (0.79 g).

(e) (S)-4-(4-Hydrazinobenzyl)-1,3-oxazolidin-2-one hydrochloride

The product from step (d) (0.79 g) was suspended in water (4.8 ml) and c.HCl (8.1 ml) added dropwise. The resulting mixture was cooled to −5° C. and a solution of sodium nitrite (0.24 g) in water (2.4 ml) added dropwise to the stirred mixture over 15 minutes followed by 30 minutes' stirring at −5 to 0° C. The solution was then added at 0° C. over 15 minutes to a stirred solution of tin (II) chloride (3.8 g) in c.HCl (6.9 ml), followed by 3 hours' stirring at room temperature. The solution was evaporated in vacuo and the residue triturated with ether to give the desired product as a pale yellow solid (0.96 g).

(f) (S)-2-[5-(2Oxo-1,3-oxazolidin-4-ylmethyl)-1H-indol-3-yl]ethylamine

The product from step (e) (0.84 g) was dissolved in ethanol/water (125 ml, 5:1) and the solution treated with 4-chlorobutanal dimethylacetal (JACS 1365 (1951), 0.52 g). The mixture was refluxed for 2 hours, the solvent removed in vacuo and the residue eluted through a silica column using DCM/EtOH/NH$_4$OH (30:8:1) as eluant. The desired product was obtained as a colourless oil (0.21 g).

Salt of Synthetic Example 1

Maleate

Ethanolic maleic acid (1.0 equiv.) was added dropwise to the free base (0.21 g) and the ethanol evaporated in vacuo. The resulting gum was freeze-dried from water to give the desired product as a white lyopholate (0.22 g), $[\alpha]_D^{21}$ −5.92° (c=0.3, MeOH).

$^1$H NMR (DMSO—d$_6$, δ): 2.7–3.5 (6H, m, CH$_2$), 3.35 (2H, s, NH$_2$), 4.05 (2H, m, CH$_2$), 4.25 (1H, m, CH), 6.05 (2H, s, maleic acid), 6.98 (1H, d, Ar), 7.2 (1H, s, Ar), 7.3 (1H, d, Ar), 7.4 (1H, s, Ar), 7.75 (1H, s, NH) and 10.9 (1H, s, NH)

Microanalysis: C 55.03 (54.96), H 5.54 (5.85), N 10.30 (10.68)

Synthetic Example 2

Preparation of (S)-N,N-dimethyl-2-[5-(2-oxo-1,3-oxazolidin-4-ylmethyl)-1H-indol-3-yl]ethylamine 0.9 isopropanolate 0.5 hydrate A solution of formaldehyde (0.03 g) in methanol (1.8 ml) was added to a solution of the free base from step (f) of Synthetic Example 1 (0.12 g) and sodium cyanoborohydride (0.04 g) in a mixture of methanol (5.5 ml) and glac. acetic acid (0.14 g) and the resulting mixture stirred overnight at room temperature. The pH was adjusted to 8.0 using aqu. K$_2$CO$_3$ and the mixture extracted with ethyl acetate. The combined extracts were washed with brine, dried and evaporated to give a colourless oil (0.14 g) which crystallised from isopropanol to give the desired product as a white crystalline solid (0.10 g), mp 139°–141° C.

$^1$H NMR (DMSO—d$_6$, δ): 2.2 (6H, s, NMe$_2$), 2.5 (2H, m, CH$_2$Ar), 2.7–3.0 (4H, m, CH$_2$), 4.1 (2H, m, CH$_2$O), 4.3 (1H, m, CH), 6.9 (1H, d, Ar), 7.1 (1H, s, Ar), 7.3 (1H, d, Ar), 7.4 (1H, s, Ar), 7.7 (1H, s, NHCO) and 10.7 (1H, s, NH).

Microanalysis: C 64.26 (64.11), H 8.28 (8.34), N 12.02 (12.00)

$[\alpha]_D^{22}$ −5.79° (c=0.5, MeOH)

Salts of Synthetic Example 2

Maleate

A solution of maleic acid (0.17 g) in ethanol (5 ml) was added to a solution of the free base (0.5 g) in ethanol (5 ml). The mixture was evaporated in vacuo and the resulting oil triturated with ether and methanol to give the maleate salt as a white solid which was recrystallised from ethanol (0.45 g), mp 151°–152° C.

Hydrochloride

Ethereal HCl (1.1 equivs.) was added dropwise to a stirred solution of the free base (0.35 g) in methanol (1 ml) at 0° C. The hydrochloride salt precipitated as an oil. The mixture was evaporated in vacuo and the resulting foam crystallised from isopropanol to give the desired product as a white solid (0.36 g), mp 118°–120° C., $[\alpha]_D^{23}$ −9.35 (c=0.31, water).

Succinate

A solution of succinic acid (0.36 g) in ethanol (10 ml) was added to a solution of the free base (1.0 g) in ethanol (10 ml). The mixture was evaporated in vacuo and the resulting foam triturated with isopropanol to give the succinate salt as a white solid (1.0 g), mp 122°–123° C.

Benzoate

A solution of benzoic acid (0.37 g) in ethanol (10 ml) was added to a solution of the free base (1.0 g) in ethanol (10 ml). The mixture was evaporated in vacuo and the resulting foam crystallised from ethyl acetate to give the benzoate salt as a white solid (0.74 g), mp 90°–92° C.

Synthetic Example 3

Alternative preparation of (S)-N,N-dimethyl-2-[5-(2-oxo-1,3-oxazo-lidinylmethyl)-1H-indol-3-yl]ethylamine 0.9 isopropanolate 0.5 hydrate 4-Dimethylaminobutanal diethylacetal (Croatica Chemica Acta 36, 103 (1964), 3.9 g) was added to a solution of the product from step (e) of Synthetic Example 1 (10.4 g) in a mixture of acetic acid (50 ml) and water (150 ml) and the resulting mixture refluxed for 4.5 hours. The mixture was cooled, evaporated in vacuo and the residue eluted through a silica column using DCM/EtOH/NH$_4$OH (50:8:1) as eluant to give the desired product as a pale yellow oil which crystallised from isopropanol as a white crystalline solid (3.5 g), mp 138°–140° C. $^1$H NMR, microanalysis and $[\alpha]_D$ as for product of Synthetic Example 2.

Synthetic Example 4

Preparation of (±)-3-(1-methyl-4-piperidyl)-5-(2-oxo-1,3-oxazolidin-4-yl-methyl)-1H-indole (a) 3-(1-Methyl-1,2,3,6-tetrahydro-4-pyridyl)-1H-indole-5-carbonitrile 5-Cyanoindole (Aldrich, 20.0 g) was added to a solution of KOH (22.4 g) in methanol (200 ml). N-Methyl-4-piperidone (Aldrich, 40.4 g) was then added dropwise and the resulting mixture refluxed for 4 hours, then cooled and poured into water. The resulting precipitate was filtered off and dried to give the desired product as a pale pink crystalline solid (32.6 g).

(b) 3-(1-Methyl-1,2,3,6-tetrahydro-4-pyridyl)-1H-indole-5-carbaldehyde

Raney nickel (ca 10 g) was added to a solution of the product from step (a) (5.0 g) and sodium hypophosphite (6.0 g) in a mixture of water (25 ml), glac. acetic acid (25 ml) and pyridine (50 ml) at 45° C. The resulting mixture was stirred at 45° C. for 1 hour, cooled and basified to pH 9 with 0.88 NH$_4$OH. The mixture was filtered through Hyflo and the filtrate extracted with chloroform. The combined extracts were dried and evaporated in vacuo to give the desired product as an off-white solid which was recrystallised from ethanol (2.4 g).

(c) 5-[3-(1-Methyl-1,2,3,6-tetrahydro-4-pyridyl)-1H-indol-5-ylmethylene]-2,4-imidazolidinedione A mixture of the product from step (b) (2.4 g), hydantoin (Aldrich, 0.98 g) and ammonium acetate (0.74 g) in glac. acetic acid (2.4 ml) was heated at 120° C. for 4 hours. The mixture was cooled and the resulting precipitate filtered off and dried to give the desired product as a yellow solid (2.4 g).

(d) (±)-5-(2,5-Dioxo-4-imidazolidinylmethyl)-3-(1-methyl-4-piperidyl)-1H-indole

The product from step (c) (2.4 g) was suspended in a mixture of water (100 ml) and ethanol (200 ml) and 10% w/w Pd/C (0.25 g) added. The mixture was stirred under 1 atoms. pressure of hydrogen for 17 hours when uptake was complete. The mixture was filtered through Hyflo and the filtrate evaporated in vacuo to give the desired product as a colourless solid (2.4 g).

(e) (±)-3-[3-(1-Methyl-4-piperidyl)-1H-indol-5-yl]alanine

A solution of the product from step (d) (2.4 g) and barium hydroxide hydrate (8.4 g) in water (50 ml) was refluxed for 72 hours, then cooled and evaporated in vacuo. The residue was taken up in hot methanol and filtered to remove barium salts. The filtrate was evaporated in vacuo, the residue dissolved in water and dry ice added to precipitate barium carbonate. The latter was filtered off and the filtrate evaporated in vacuo to give the desired product as a yellow foam (1.3 g).

(f) (±)-Methyl 3-[3-(1-methyl-4-piperidyl)-1H-indol-5-yl]alanate

A solution of the product from step (e) (6.2 g) in methanol (40 ml) was added dropwise to a solution of thionyl chloride (2.9 ml) in methanol (35 ml) at −10° C. The resulting mixture was stirred overnight at room temperature, then evaporated in vacuo and the residue eluted through a silica column using DCM/EtOH/N-H$_4$OH (30:8:1) as eluant. The eluate was evaporated in vacuo to give the desired product as a yellow foam (4.8 g).

(g) (±)-3-[3-(1-Methyl-4-piperidyl)-1H-indol-5-yl]-2-amino-1-propanol

A solution of the product from step (f) (4.8 g) in water (20 ml) and ethanol (20 ml) was added dropwise to a suspension of sodium borohydride (0.61 g) in a mixture of water (20 ml) and ethanol (20 ml) at 0° C. The resulting mixture was refluxed for 3 hours then evaporated in vacuo and the residue eluted through a silica column using DCM/EtOH/NH$_4$OH (30:8:1) as eluant. The eluate was evaporated in vacuo to give the desired product as a colourless foam (1.6 g).

(h) (±)-3-(1-Methyl-4-piperidyl)-5-(2-oxo-1,3-oxazolidin-4-ylmethyl)-1H-indole

A mixture of the product from step (g) (1.6 g), diethyl carbonate (0.73 ml) and potassium carbonate (0.08 g) was heated at 130° C. for 5 hours. The mixture was cooled, taken up in methanol and the insoluble potassium carbonate filtered off. The filtrate was evaporated in vacuo and the residue eluted through a silica colum using DCM/EtOH/NH$_4$OH (30:8:1) as eluant. The eluate was evaporated in vacuo and the residue recrystallised from isopropanol/ether to give the desired product as a colourless crystalline solid (1.1 g), mp 191°–192° C.

$^1$H NMR (DMSO—d$_6$, δ): 1.6–1.8 (2H, 2×CHNMe), 1.8–2.1 (4H, 2×CH$_2$), 2.2 (3H, s, NMe), 2.6–3.0 (2H, 2×CHNMe; 1H, CH; 2H, CH$_2$Ar), 3.9–4.1 (2H, m, CH$_2$O), 4.2–4.4 (1H, m, CHN), 6.9 (1H, d, Ar), 7.1 (1H, d, Ar), 7.3 (1H, d, Ar), 7.4 (1H, s, Ar), 7.8 (1H, s, NHCO) and 10.7 (1H, s, NH)

Salt of Synthetic Example 4

Hydrochloride c.HCl (1.0 equiv.) was added dropwise to a stirred solution of the free base (1.1 g) in ethanol (5 ml) at 5° C. The addition of ether to the resulting mixture precipitated the desired product as a white solid (1.1 g), mp 235°–236° C. (dec).

Synthetic Example 5

Alternative preparation of (±)-3-(1-methyl-4-piperidyl)-5-(1,3-oxazolidin-4-ylmethyl)-1H-indole (a) 1H-Indole-5-carbaldehyde Raney nickel (6.7 g) was added to a solution of 5-cyanoindole (Aldrich, 10.0 g) and sodium hypophosphite (20.0 g) in a mixture of water (73 ml), glac. acetic acid (73 ml) and pyridine (145 ml) at 45° C. The resulting mixture was stirred at 45° C. for 2 hours, then cooled and filtered through Hyflo. The filtrate was diluted with water and extracted with ethyl acetate. The combined extracts were washed with water, 10% aqu. citric acid, 1N aqu. HCl, water and brine, dried and evaporated in vacuo to give the desired product as a buff solid which was recrystallised from chloroform (7.5 g).

(b) 5-(2-nitroethenyl)-1H-indole

A mixture of the product from step (a) (7.5 g), ammonium acetate (1.5 g) and nitromethane (77 ml) was heated at 110° C. for 2 hours, then cooled and evaporated in vacuo. The residue was triturated with water to give the desired product as a yellow solid which was filtered off and dried (9.2 g).

(c) 5-(2-nitroethyl)-1H-indole

A solution of sodium borohydride (2.0 g) and 40% w/v aqu. NaOH was added dropwise to a solution of the the product from step (b) (1.9 g) in acetonitrile (55 ml) at 0° C. The pH was maintained at 3–6 by periodic additions of 2N aqu. HCl. The resulting solution was stirred at 0° C. for 2 hours, then diluted with water and extracted with DCM. The combined extracts were washed with brine, dried and evaporated in vacuo to give a yellow oil which was eluted through a silica column using chloroform as eluant to give the desired product as a pale yellow oil (0.78 g).

(d) 3-(1-Methyl-1,2,3,6-tetrahydro-4-pyridyl)-5-(2-nitroethyl)-1H-indole

N-Methyl-4-piperidone (Aldrich, 4.2 g) was added to a solution of the product from step (c) (2.3 g) in glac. acetic acid (35 ml) at 100° C. The resulting solution was heated at 100° C. for 1 hour, cooled and poured into a mixture of 0.88 NH$_4$OH (61 ml) and ice (61 g). The resulting solid was filtered off, dried and recrystallised from ethanol to give the desired product as a white solid (1.6 g).

(e) (±)-3-[3-(1-Methyl-1,2,3,6-tetrahydro-4-pyridyl)-1H-indol-5-yl]-2-amino-1-propanol Sodium methoxide (0.30 g) was added to a solution of the product from step (d) (1.5 g) in DMF (15 ml) at 0° C. To the resulting solution was added dropwise a suspension of paraformaldehyde (0.19 g) in DMF (20 ml). The resulting mixture was stirred at 0° C. for 1.5 hours, then poured into water and extracted with ethyl acetate. The combined extracts were washed with water and brine, dried and evaporated in vacuo to give a yellow oil which was eluted through a silica column using DCM/EtOH/NH$_4$OH (50:8:1) as eluant to give the desired product as an off-white solid (0.85 g) which was recrystallised from ethanol.

(f) (±)-3-[3-(1-Methyl-4-piperidyl)-1H-indol-5-yl]-2-amino-1-propanol

The product from step (e) (0.08 g) was dissolved in ethanol (25 ml) and 10% w/w Pd/C (0.23 g) added. The mixture was stirred under 1 atmos. pressure of hydrogen for 7 hours when uptake was complete. The mixture was filtered through celite and the filtrate evaporated in vacuo to give the desired product as colourless oil which was eluted through a silica column using DCM/EtOH/NH$_4$OH (50:8:1) as eluant.

(g) (±)-3-(1-Methyl-4-piperidyl)-5-(1,3-oxazolidin-4-ylmethyl)-1H-indole

A mixture of the product from step (f) (1.6 g), diethyl carbonate (0.71 g) and potassium carbonate (0.08 g) was heated at 130° C. for 5 hours. The mixture was cooled, taken up in methanol and the insoluble potassium carbonate filtered off. The filtrate was evaporated in vacuo and the residue eluted through a silica column using DCM/EtOH/NH$_4$OH (30:8:1) as eluant to give a colourless foam which was crystallised from isopropanol/ether to give the desired product as a colourless crystalline solid (1.1 g), mp 191°–192° C. $^1$H NMR and microanalysis as for product of Synthetic Example 4.

Synthetic Example 6

Preparation of (R)-2-[5-(2-oxo-1,3-oxazolidin-4-ylmethyl)-1H-indol-3-yl]ethylamine (a) (R)-4-(4-nitrobenzyl)-1,3-oxazolidin-2-one A solution of D-4-nitrophenylalanine (Fluka, 53 g) in dimethoxyethane (250 ml) was warmed to 67° C. and BF$_3$.Et$_2$O (Aldrich, 37 ml) added over 1 hour. The resulting solution was stirred at 67° C. for 1 hour, then heated to 80° C. and BH$_3$.Me$_2$S (Aldrich, 40 ml) added over 1 hour at 80°–85° C. The resulting solution was heated at 85° C. for 4 hours, then cooled and methanol (40 ml) added. The solution was heated to 85° C. and the solvents removed by distillation to ½ of the original bulk. 6N aqu. NaOH (136 ml) was added to the hot solution which was then heated at 85° C. for ½ hour, cooled and DCM (100 ml) added. The solution was cooled to −15° to −20° C. and a solution of trichloromethyl chloroformate (Aldrich, 18.2 ml) in DCM (23 ml) added at below −10° C. The pH was maintained at 9–11 by periodic additions of 6N aqu. NaOH. The resulting solution was stirred at room temperature for 1 hour, then diluted with water and extracted with DCM. The combined extracts were washed with water and brine, dried and evaporated in vacuo to give the desired product as a pale brown solid which was recrystallised from ethyl acetate to give a pale yellow solid (35 g), mp 113°–115°, $[\alpha]_D^{21}$+46.47° (c=0.56. MeOH).

(b) (R)-4-(4-Aminobenzyl)-1,3-oxazolidin-2-one hydrochloride

The product from step (a) (10.0 g) was suspended in a mixture of water (120 ml), ethanol (60 ml) and 2N aqu. HCl (22.5 ml) and 10% w/w Pd/C (1.0 g) added. The mixture was stirred under 1 atmos. pressure of hydrogen for 8 hours when uptake was complete. The mixture was filtered through Hyflo and the filtrate evaporated in vacuo to give the desired product as a colourless glass (10.3 g).

(c) (R)-4-(4-Hydrazinobenzyl)-1,3-oxazolidin-2-one hydrochloride

The product from step (b) (10.3 g) was suspended in water (53 ml) and c.HCl (106 ml) added dropwise. The resulting mixture was cooled to −5° C. and a solution of sodium nitrite (3.2 g) in water (30 ml) added dropwise to the stirred mixture over 15 minutes followed by 30 minutes' stirring at −5° to 0° C. The solution was then added at 0° C. over 15 minutes to a stirred solution of tin (II) chloride (51 g) in c.HCl (91 ml), followed by 3 hours' stirring at room temperature. The solution was evaporated in vacuo and the residue triturated with ether to give the desired product as a pale yellow solid (11 g).

(d) (R)-2-[5-(2-Oxa-1,3-oxazolidin-4-ylmethyl)-1H-indol-3-yl]-ethylamine

The product from step (c) (8.8 g) was dissolved in ethanol/water (500 ml, 5:1 v/v) and the solution treated with 4-chlorobutanal dimethylacetal (J. Amer. Chem. Soc. 1365 (1951), 5.5 g). The mixture was refluxed for 2 hours, the solvent removed in vacuo and the residue eluted through a silica column using DCM/EtOH/NH$_4$OH (30:8:1 v/v/v) as eluant. The desired product was obtained as a pale yellow oil (0.60 g).

Salt of Synthetic Example 6

Hydrochloride c.HCl (0.06 ml) was added dropwise to a stirred solution of the free base (0.16 g) in ethanol (2 ml) at 0° C. The hydrochloride salt was precipitated as a fawn solid, mp 269°–271° C., $[\alpha]_D^{21}$+5.88° (c=0.27. MeOH).

Synthetic Example 7

Preparation of
(R)-N,N-dimethyl-2-[5-(2-oxo-1,3-oxazolidin-4-ylmethyl)-1H-indol-3-yl]ethylamine A solution of 35% w/v aqu. formaldehyde (0.3 ml) in methanol (2.0 ml) was added to a solution of the product from step (d) of Synthetic Example 6 (0.44 g) and sodium cyanoborohydride (0.13 g) in a mixture of methanol (8.5 ml) and glac. acetic acid (0.51 g) at 10° C. and the resulting mixture stirred at room temperature for 2.5 hours. 2N aqu. NaOH (1.3 ml) was added, then sodium borohydride (0.19 g) followed by 2N aqu. HCl (1.3 ml). The methanol was evaporated in vacuo and the remaining solution diluted with water, taken to pH 7 with solid potassium carbonate and washed with ethyl acetate. Further potassium carbonate was added to pH 11 and the solution extracted with ethyl acetate. The combined extracts were evaporated in vacuo to give the desired product as a white foam (0.45 g).

Salt of Synthetic Example 7

Hydrochloride c.HCl (0.16 ml) was added dropwise to a stirred solution of the free base (0.45 g) in ethanol (4.5 ml) at 0° C. The mixture was evaporated in vacuo and the resulting foam triturated with ethyl acetate to give the desired product as a white solid, mp 130° C., $[\alpha]_D^{21}$+5.15° (c=0.77, MeOH).

Synthetic Example 8

Preparation of
(S)-N,N-dimethyl-2-[5-(2-thia-1,3-oxazolidin-4-ylmethyl)-1H-indol-3-yl]ethylamine hydrochloride (a) (S)-N,N-Dimethyl-2-[5-(2-amino-1-propanol)-1H-indol-3-yl]ethylamine A solution of the hydrochloride salt of the product of Synthetic Example 2 (0.33 g) in 2N aqu. KOH (10 ml) was refluxed for 4 hours, then cooled and extracted with ethyl acetate. The combined extracts were dried and evaporated in vacuo to give the desired product as a colourless oil (0.25 g).

(b) (S)-N,N-Dimethyl-2-[5-(2-thia-1,3-oxazolidin-4-ylmethyl)-1H-indol-3-yl]ethylamine hydrochloride A solution of N,N'-thiocarbonylimidazole (Aldrich, 0.21 g) in THF (4 ml) was added dropwise to a stirred solution of the product from step (a) (0.31 g) in THF (4 ml) and the mixture refluxed for 23 hours, then cooled and evaporated in vacuo. The residue was chromatographed through a silica column using DCM/EtOH/NH$_4$OH (20:8:1) as eluant to give the desired product as a colourless oil.

Salt of Synthetic Example 8

Hydrochloride

1M Ethanolic HCl (1.0 equiv.) was added dropwise to the free base and the ethanol evaporated in vacuo. The resulting gum was freeze-dried from water to give the desired product as a white solid (0.17 g). mp 133°–136° C. (softens 128° C.), $[\alpha]_D^{24.5}$−29.8° (c=0.5, water).

Synthetic Example 9

Preparation of
(S)-2-[5-(3-methyl-2-oxo-1,3-oxazolidin-4-ylmethyl-1H-indol-3-yl]ethylamine hydrobromide (a) (S)-3-Methyl-4-(4-nitrobenzyl)-2-oxazolidinone Sodium hydride (0.80 g as a 60% w/w dispersion in oil) was added at room temperature to a stirred solution of the product from step (c) of Synthetic Example 1 (4.4 g) in dry THF (150 ml). The mixture was stirred for 1.5 hours, then dimethyl sulphate (2.1 ml) was added and stirring continued for a further 16 hours. More sodium hydride (0.40 g) was added and stirring continued for another 2 hours. The mixture was evaporated in vacuo and the residue suspended in ethyl acetate and filtered. The filtrate was evaporated in vacuo and the residue crystallised from ethyl acetate/hexane to give the desired product as yellow crystals (3.7 g), mp 146°–147° C., $[\alpha]_D^{23}$ +64.5° (c=1.0, MeOH).

(b) (S)-3-Methyl-4-(4-aminobenzyl)-2-oxazolidinone hydrochloride

A suspension of the product from step (a) (4.0 g) and 10% w/w Pd/C (0.20 g) in a mixture of ethanol (70 ml) and dil. HCl (2N aqu. HCl (12 ml)+water (55 ml)) was hydrogenated at 45 psi for 1 hour. The mixture was filtered through Hyflo and the filtrate evaporated in vacuo to give the desired product as a foam.

(c) (S)-3-Methyl-4-(4-hydrazinobenzyl)-2-oxazolidinone hydrochloride

A solution of the product from step (b) (4.1 g) in water (24 ml) was cooled to −5° C. and c.HCl (40 ml) added. A solution of sodium nitrite (1.2 g) in water (12 ml) was then added and stirring continued for 0.5 hour. The resulting solution was added dropwise at −5° C. to a stirred solution of stannous chloride dihydrate (18.8 g) in c.HCl (34 ml). The resulting mixture was stirred at 0° C. for 2.5 hours, then evaporated in vacuo. The residue was taken up in water, brought to pH 2.5 using 10N aqu. NaOH and filtered. The filtrate was evaporated in vacuo and the residue triturated with ethanol and filtered. The filtrate was evaporated in vacuo to give the desired product as a froth.

(d) (S)-2-[5-(3-Methyl-2-oxo-1,3-oxazolidin-4-ylmethyl)-1H-indol-3-yl]ethylamine hydrobromide 4-Chlorobutanal dimethylacetal (J. Amer. Chem. Soc. 1365 (1951), 2.3 g) was added to a stirred solution of the product from step (c) (4.4 g) in ethanol/water (150 ml/30 ml) and the mixture refluxed for 2 hours. The cooled mixture was evaporated in vacuo and the residue eluted through a silica column using DCM/MeOH/NH$_4$OH (60:8:1) as eluant to give a brown oil (1.7 g). A portion of this (0.25 g) was taken up in ethanol and treated with an excess of HBr in acetic acid (ca 45% w/v). The resulting solution was evaporated in vacuo and the residue triturated with ether, then crystallised from ethanol/hexane to give the desired product as pale yellow crystals (0.14 g), mp 203°–205° C., $[\alpha]_D^{25}$ +29.9° (c=0.5, MeOH). Elemental analysis and $^1$H NMR were consistent with the proposed structure.

Synthetic Example 10

Preparation of (S)-N,N-dimethyl-2-[5-(3-methyl-2-oxo-1,3-oxazolidin-4-ylmethyl)-1H-indol-3-yl]ethylamine maleate 0.75 hydrate Sodium cyanoborohydride (0.14 g) followed by glac. acetic acid (0.54 ml) were added at room temperature to a stirred solution of the free base (0.52 g) from step (d) of Synthetic Example 9 in methanol (9.0 ml). When effervescence was complete, a solution of 37% w/v aqu. formaldehyde (0.16 g) in methanol (2.0 ml) was added and the mixture stirred for 1 hour, then diluted with water, saturated with potassium carbonate and extracted with ethyl acetate. The combined extracts were evaporated in vacuo and the residue eluted through a silica column using DCM/MeOH/NH$_4$OH (60:8:1) as eluant to give the free base of the desired product as a colourless oil (0.25 g). The latter was dissolved in ethanol (10 ml), treated with a solution of maleic acid (0.09 g) in ethanol (1 ml) and the resulting solution evaporated in vacuo to give an oil which was triturated with ether, then freeze-dried from water to give the desired product as a colourless glass, $[\alpha]_D^{22}$+24.5° (c=0.5. MeOH). Elemental analysis. $^1$H NMR and MS were consistent with the proposed structure.

Synthetic Example 11

Preparation of (S)-N-benzyl-2-[5-(2-oxo-1,3-oxazolidin-4-ylmethyl)-1H-indol-3-yl]ethylamine maleate 0.75 hydrate Benzaldehyde (0.70 g) was added at room temperature to a stirred solution of the compound of Synthetic Example 1 (1.7 g) in ethanol (20 ml). The solution was stirred for 36 hours, then sodium borohydride (0.25 g) was added in portions and stirring continued for a further 2 hours. The solution was evaporated in vacuo and the residue cooled, acidified with 2N aqu. HCl, basified with sodium bicarbonate, saturated with potassium carbonate and extracted with ethyl acetate. The combined extracts were evaporated in vacuo to give an oil which was eluted through a silica column using DCM/EtOH/NH$_4$OH (100:8:1) as eluant to give the free base of the desired product as a yellow froth (1.6 g). A portion of this (0.13 g) was dissolved in ethanol 10 ml), treated with a solution of maleic acid (43 mg) in ethanol (1 ml) and the resulting solution evaporated in vacuo. The residue was freeze-dried from water to give the desired product as a pale yellow powder (0.16 g), $[\alpha]_D^{24}$ +1.4° (c=0.5, MeOH). Elemental analysis, $^1$H NMR and MS were consistent with the proposed structure.

Synthetic Example 12

Preparation of (S)-N-benzyl-N-methyl-2-[5-(2-oxo-1,3-oxazolidin-4-ylmethyl)-1H-indol-3-yl]ethylamine maleate hydrate Anhy. potassium carbonate (0.34 g) was added at room temperature to a solution of the free base of Synthetic Example 11 (0.45 g) in DMF (8.0 ml). The suspension was stirred for 0.5 hour, then a solution of dimethyl sulphate (0.17 g) in DMF (2.0 ml) was added and stirring continued for a further 3 hours. Water (40 ml) was added and the mixture extracted with ethyl acetate. The combined extracts were evaporated in vacuo to give a yellow oil which was eluted through a silica column using DCM/EtOH/NH$_4$OH (100:8:1) as eluant to give the free base of the desired product as a colourless oil (0.32 g). A portion of this (73 mg) was dissolved in ethanol (10 ml), treated with a solution of maleic acid (23 mg) in ethanol (1 ml) and the resulting solution evaporated in vacuo. The residue was freeze-dried from water to give the desired product as a pale yellow powder, $[\alpha]_D^{24}$ +3.1° (c=0.5, MeOH). Elemental analysis, $^1$H NMR and MS were consistent with the proposed structure.

Synthetic Example 13

Preparation of (S)-N-methyl-2-[5-(2-oxo-1,3-oxazolidin-4-ylmethyl)-1H-indol-3-yl]ethylamine maleate 0.5 hydrate A suspension of the free base of the product of Synthetic Example 12 (0.25 g) and 10% w/w Pd/C (0.10 g) in ethanol (25 ml) was hydrogenated for 16 hours. The mixture was filtered through Hyflo and the filtrate evaporated in vacuo. The residue was eluted through a silica column using DCM/EtOH/NH$_4$OH (30:8:1) as eluant to give the free base of the desired product (0.14 g). The latter was dissolved in ethanol (10 ml). treated with a solution of maleic acid (0.06 g) in ethanol (1 ml) and the resulting solution evaporated in vacuo. The residue was freeze-dried from water to give the desired product as a hygroscopic solid, $[\alpha]_D^{25}$ −5.4° (c=0.5, MeOH). Elemental analysis and $^1$H NMR were consistent with proposed structure.

Synthetic Example 14

Preparation of (S)-3-(1-methyl-1,2,3,6-tetrahydro-4-pyridyl)-5-(2-oxo-1,3-oxazolidin-4-ylmethyl)-1H-indole 0.33 methanolate 0.75 hydrate (a) (S)-3-Phenylthio-5-(2-oxo-1,3-oxazolidin-4-ylmethyl)-1H-indole Phenylthioacetaldehyde diethylacetal (JCS, Chem. Comm. 924 (1978), 9.1 g) was added at room temperature to a stirred solution of the product from step (e) of Synthetic Example 1 (9.8 g) in a mixture of ethanol (150 ml) and water (100 ml). c.HCl (5 drops) was added and the mixture stirred at room temperature for 2 days, then partially evaporated in vacuo. The resulting aqueous suspension was extracted with ethyl acetate and the combined extracts washed with water and evaporated in vacuo to give a brown oil. The latter was eluted through a silica column using DCM/Etoh/NH$_4$OH (150:8:1) as eluant to give the desired product as a pale yellow oil (5.0 g).

(b) (S)-5-(2-oxo-1,3-oxazolidin-4-ylmethyl)-1H-indole

Raney nickel (3.0 g) was added to a solution of the product from step (a) (3.1 g) in IPA (150 ml) and the suspension refluxed for 1 hour. More Raney nickel (2.0 g) was added and refluxing continued for a further 2 hours. The suspension was filtered hot through Hyflo and the filtrate evaporated in vacuo to give an oil. The latter was eluted through a silica column using ethyl acetate as eluant to give the desired product as a froth (1.3 g). $^1$H NMR and MS were consistent with the proposed structure.

(c) (S)-3-(1-Methyl-1,2,3,6-tetrahydro-4-pyridyl)-5-(2-oxo-1,3-oxazolidin-4-ylmethyl)-1H-indole 0.33 methanolate 0.75 hydrate 1-Methyl-4-piperidone (0.47 g, Aldrich) was added to a stirred solution of the product from step (b) (0.30 g) in glac. acetic acid (2.0 ml) and the mixture stirred at 100° C. for 2 hours. The cooled mixture was poured onto ice/NH$_4$OH (20 ml) and the resulting solid filtered off. The latter was eluted through a silica column using DCM/EtOH/NH$_4$OH (60:8:1) as eluant and crystallised from ethyl acetate to give the desired product as a colourless solid (0.11 g), mp 225°-227° C., $[\alpha]_D^{20}$ −45.4° (c=0.5. 1N aqu. HCl). Elemental analysis and $^1$H NMR were consistent with the proposed structure.

Synthetic Example 15

Preparation of (S)-3-(1-methyl-4-piperidyl)-5-(2-oxo-1,3-oxazolidin-4-ylmethyl)-1H-indole hydrobromide A suspension of the product of Synthetic Example 14 (0.35 g) and 10% w/w Pd/C (0.10 g) in a mixture of methanol (10 ml), water (10 ml) and 1N aqu. HCl was hydrogenated for 5 hours. The mixture was filtered through Hyflo and the filtrate evaporated in vacuo. The residue was basified with NH$_4$OH, evaporated in vacuo and eluted through a silica column using DCM/EtOH/NH$_4$OH (45:8:1) as eluant to give an oil. The latter was taken up in ethanol (5.0 ml) and treated with an excess of HBr in acetic acid (ca 45% w/v) to give the desired product as colourless crystals (0.20 g), mp 260°-261° C., $[\alpha]_D^{21}$ −5.2° (c=0.5. water). Elemental analysis and $^1$H NMR were consistent with the proposed structure.

Synthetic Example 16

Preparation of (R)-3-(1-methyl-1,2,3,6-tetrahydro-4-pyridyl)-5-(2-oxo-1,3oxazolidin-4-ylmethyl)-1H-indole hydrate (a) (R)-4-(4-Hydrazinobenzyl)-1,3-oxazolidin-2-one hydrochloride By steps identical to steps (a) to (c) of Synthetic Example 6, D-4-nitrophenylalanine was converted to (R)-4-(4-hydrazinobenzyl)-2-oxazolidinone hydrochloride.

(b) (R)-3-(1-Methyl-1,2,3,6-tetrahydro-4-pyridyl)-5-(2-oxo-1,3-oxazolidin-4-yl)-1H-indole hydrate By steps analogous to steps (a) to (c) of Synthetic Example 14, the product from step (a) was converted to (R)-3-(1-methyl-1,2,3,6-tetrahydro-4-pyridyl)-5-(2-oxo-1,3-oxazolidin-4-ylmethyl)-1H-indole hydrate, mp 229°-231° C., $[\alpha]_D^{18}$ +24.9° (c=0.5, 1N aqu. HCl). Elemental analysis and $^1$H NMR were consistent with the proposed structure.

Synthetic Example 17

Preparation of (R)-3-(1-methyl-4-piperidyl)-5-(2-oxo-1,3-oxazolidin-4-ylmethyl)-1H-indole hydrobromide By a method analogous to that of Synthetic Example 15, the product of Synthetic Example 16 was converted to (R)-3-(1-methyl-4-piperidyl)-5-(2-oxo-1,3-oxazolidin-4-ylmethyl)-1H-indole hydrobromide, mp 260°-261° C., $[\alpha]_D^{19}$ +4.6° (c=0.5, water). Elemental analysis and $^1$H NMR were consistent with the proposed structure.

Synthetic Example 18

Preparation of (R)-3-(1-benzyl-1,2,3,6-tetrahydro-4-pyridyl)-5-(2-oxo-1,3-oxazolidin-4-ylmethyl)-1H-indole hydrate 1-Benzyl-4-piperidone (Aldrich, 2.8 g) was added to a stirred suspension of (R)-5-(2-oxo-1,3-oxazolidin-4-ylmethyl)-1H-indole (1.0 g), the immediate precursor of the product of Synthetic Example 16, in glac. acetic acid (20 ml) and stirred at 100° C. for 3 hours. The cooled mixture was evaporated in vacuo and the residue taken up in methanol, basified with NH$_4$OH and evaporated in vacuo to give a dark tar. The latter was eluted through a silica column using DCM/EtOH/NH$_4$OH (100:8:1) as eluant and treated with DCM. The resulting precipitate was filtered off to give the desired product as yellow crystals (0.25 g), mp 169°-170.5° C. Elemental analysis and $^1$H NMR were consistent with the proposed structure.

Synthetic Example 19

Preparation of (R)-3-(4-piperidyl)-5-(2-oxo-1,3-oxazolidin-4-ylmethyl)-1H-indole hydrobromide A suspension of the product from Synthetic Example 18 (0.25 g) and 10% w/w Pd/C (0.10 g) in methanol (25 ml) was hydrogenated at 90 psi for 20 hours when uptake ceased. The mixture was filtered through Hyflo and the filtrate evaporated in vacuo. The residue was eluted through a silica column using DCM/EtOH/NH$_4$OH (30:8:1) as eluant to give an oil. The latter was taken up in IPA and treated with an excess of HBr in acetic acid (ca 45% w/v) to give a hygroscopic solid which was freeze-dried from water to give the desired product as a pale brown powder. Elemental analysis and $^1$H NMR were consistent with the proposed structure.

Synthetic Example 20

Preparation (±)-N,N-dimethyl-2-[5-(1-thio-2-thia-3-oxazolidin-4-ylmethyl)-1H-indol-3-yl]ethylamine acetate Carbon disulphide (90 μl) was added to a stirred solution of the product from step (a) of Synthetic Example 8 (0.31 g) and potassium hydroxide (0.08 g) in ethanol (3.8 ml) and the mixture refluxed, then evaporated in vacuo. The residue was extracted with ether, acidified and chromatographed using a silica reverse phase HPLC column and eluting with 10→90% v/v water-/acetonitrile with 0.1M aqu. ammonium acetate buffer at pH 4.0 over 20 minutes to give the desired product (0.01 g) and, after treatment with HCl, the product of Synthetic Example 8 (0.11 g). Both were freeze-dried from water and gave $^1$H NMR and MS which were consistent with the proposed structures.

Synthetic Example 21

Preparation of
(±)-N,N-dimethyl-2-[5-(2-oxo-2,3-oxazolidin-5-ylmethyl)-1H-indol-3-yl]ethylamine hydrochloride (a) (±)-1-Nitromethyl-2-phenylethanol Sodium methoxide (1.1 g) was added to a stirred solution of nitromethane (Aldrich, 12.2 g) in methanol (100 ml) at 0° C. and the mixture stirred for 10 minutes. A solution of phenylacetaldehyde (Aldrich, 24.0 g) in methanol (50 ml) was added dropwise over 15 minutes and the mixture stirred for 45 minutes at 0° C., then brought to room temperature over 1 hour and stirred overnight. The mixture was evaporated in vacuo and the residue taken up in water and extracted with ether. The combined extracts were washed with water and brine and evaporated in vacuo to give the desired product as a yellow oil (29.0 g).

(b) (±)-1-Aminomethyl-2-phenylethanol hydrochloride

A suspension of the product from step (a) (10.0 g) and 10% w/w Pd/C (1.0 g) in ethanol (250 ml) was hydrogenated until uptake ceased. The mixture was filtered through Hyflo and the filtrate evaporated in vacuo. The residue was taken up in ethyl acetate and extracted with 2N aqu. HCl. The combined extracts were washed with ethyl acetate, then evaporated in vacuo to give the desired product as a pinkish white solid (6.8 g).

(c) (±)-5-Benzyl-1,3-oxazolidin-2-one

A solution of KOH (9.4 g) in water (85 ml) was added to a stirred solution of the product from step (b) (5.1 g) in toluene (150 ml) at 0° C. A solution of phosgene (9.8 g) in toluene (78.4 ml 12.5% w/v) was added dropwise over 15 minutes and the mixture brought to room temperature, then stirred overnight. The aqueous phase was separated and extracted with ethyl acetate. The combined extracts were evaporated in vacuo to give the desired product as a white solid (2.2 g), mp 106°–108° C. Elemental analysis was consistent with the proposed structure.

(d) (±)-5-(4-Nitrobenzyl)-1,3-oxazolidin-2-one c.H$_2$SO$_4$ (1.6 ml) was added to the product from step (c) at 0° C. followed by c.HNO$_3$ (0.33 ml, ca 0.05 ml/5 minutes) also at 0° C. The mixture was stirred for 0.5 hour at 0° C. and then for 0.5 hour at room temperature. Water/ice (100 ml) was added and the mixture extracted with ethyl acetate. The combined extracts were evaporated in vacuo to give a yellow oil which was recrystallised from ethyl acetate to give the desired product as a white powder (0.4 g), mp 143°–146° C.

(e) (±)-5-(4-Aminobenzyl)-1,3-oxazolidin-2-one hydrochloride

A suspension of the product from step (d) (1.4 g) and 10% w/w Pd/C (0.14 g) in a mixture of water (21 ml), ethanol (28 ml) and 2N aqu. HCl (3.2 ml) was hydrogenated for 2 hours when uptake ceased. The mixture was filtered through Hyflo and the filtrate evaporated in vacuo to give the desired product as a pale yellow foam (1.4 g).

(f) (±)-N,N-Dimethyl-2-[5-(2-oxo-1,3-oxazolidin-5-ylmethyl)-1H-indol-3-yl]ethylamine hydrochloride c.HCl (14.5 ml) was added to a stirred solution of the product from step (e) (1.4 g) in water (8.5 ml) at 0° C. A solution of sodium nitrite (0.43 g) in water (4.3 ml) was added dropwise over 15 minutes at 0° C. and the mixture stirred for 0.5 hour at 0° C. The mixture was then added dropwise to a stirred solution of tin (II) chloride (6.8 g) in c.HCl (12.4 ml) at 0° C. over 15 minutes. The mixture was brought to room temperature over 1 hour, then evaporated in vacuo. The residue was taken up in water (30 ml). brought to pH 2.5 using 10N aqu. NaOH and the precipitated salts filtered off. 4-Dimethylaminobutanal diethylacetal (Croatica Chemica Acta 36, 103 (1964), 1.1 g) followed by 'Amberlyst 15'ion exchange resin (Aldrich, 3.0 g) was added to the filtrate and the mixture heated for 3 hours at 100° C., filtered and the filtrate evaporated in vacuo. The residue was treated with hot ethanol, filtered and the filtrate evaporated in vacuo. The residue was triturated with ethyl acetate, filtered and the filtrate evaporated in vacuo. The residue was recrystallised from ethanol to give the desired product as a pale yellow solid (0.75 g), mp 280°–281° C. $^1$H NMR and MS were consistent with the proposed structure.

Synthetic Example 22

Preparation of
(S)-N,N-dimethyl-2-[5-(2-oxo-1,3-oxazolidin-4-ylmethyl)-1H-indol-3-yl]ethylamine (a) (S)-5-(4-Nitrobenzyl)-1,3-imidazolidin-2,4-dione Benzyl isocyanate (Aldrich, 3.2 g) was added to a solution of L-4-nitrophenylalanine (Aldrich. 4.2 g) and potassium hydroxide (1.3 g) in water (40 ml) at 0° c. The mixture was heated at 60°–70° C. for 2 hours, filtered and the filtrate acidified with c.HCl to give and off-white solid which was filtered off. suspended in 2N aqu. HCl (20 ml) and refluxed for 2 hours. The cooled mixture was diluted with water and filtered to give the desired product as a white solid (5.6 g)

(b) (S)-N,N-Dimethyl-2-[5-(2-oxo-1,3-oxazolidin-4-ylmethyl)-1H-indol-3-yl]ethylamine By steps identical to steps (d) to (f) of Synthetic Example 1 and Synthetic Example 2 or steps (d) and (e) of Synthetic Example 1 and Synthetic Example 3 and steps (e) to (h) of Synthetic Example 4, the product from step (a) was converted to (S)-N,N-diemthyl-2-[5-(2-oxo-1,3-oxazolidin-4-ylmethyl)-1H-indol-3-yl]ethylamine.

Synthetic Example 23

Preparation of
(S)-N,N-dimethyl-2-[5-(2-oxo-1,3-oxazolidin-4-ylmethyl)-1H-indol-3-yl]ethylamine (a) (S)-4-(4-Hydrazinobenzyl)-1,3-oxazolidin-2-one hydrochloride By steps analogous to steps (a) to (c) of Synthetic Example 6, L-4-nitrophenylalanine was converted to (S)-4-(4-hydrazinobenzyl)-1,3-oxazolidin-2-one hydrochloride.

(b) (S)-4-{4-[2-(3-cyanopropylidene)hydrazino]benzyl}-1,3-oxazolidin-2-one 1M aqu. HCl (4.0 ml) was added to a solution of the product from step (a) (2.4 g) in water (35 ml). 3-Cyanopropanal diethylacetal (Aldrich, 1.7 g) was added at room temperature and the mixture stirred for 2 hours. Further acetal (0.20 g) was added and the mixture stirred for another 20 minutes. The aqueous phase was decanted from the resulting gum and extracted with ethyl acetate. The extracts were combined with the gum and evaporated in vacuo to give the desired product (2.5 g).

(c) (S)-3-Cyanomethyl-5-(2-oxo-1,3-oxazolidin-4-ylmethyl)-1H-indole

A solution of the product from step (b) (2.5 g) and polyphosphate ester (20.0 g) in chloroform (40 ml) was refluxed for 20 minutes. Ice was added to the cooled mixture and the chloroform evaporated in vacuo. The remaining aqueous phase was extracted with ethyl acetate and the combined extracts evaporated in vacuo to give the desired product as a pale yellow oil (1.8 g).

(d) (S)-N,N-Dimethyl-2-[5-(2-oxo-1,3-oxazolidin-4-ylmethyl)-1H-indol-3-yl]ethylamine A suspension of the product from step (c) (1.3 g) and 10% w/w Pd/C (1.0 g) in 30% w/w ethanolic dimethylamine (25 ml) was hydrogenated for 24 hours and filtered through Hyflo. Fresh Pd/C (0.7 g) and ethanolic dimethylamine (5 ml) were added to the filtrate and hydrogenation continued for a further 16 hours. The mixture was filtered through a silica column using DCM/EtOH/NH$_4$OH (40:8:1) as eluant to give the desired product as a colourless foam (0.3 g). Elemental analysis and $^1$H NMR were consistent with the proposed structure.

Synthetic Examples 24 to 31

By methods analogous to those described in Synthetic Examples 1 to 23, the following compounds of formula (I) were prepared. The NMR and microanalysis for each compound were consistent with the proposed structure.

24) 2-[5-(3-Methyl-2-oxoimidazolidin-4-ylmethyl)-1H-indol-3-yl]ethylamine maleate 0.75 hydrate, mp 94°–98° C.;

25) 2-[5-(3-Methyl-2-oxoimidazolidin-4-ylmethyl)-1H-indol-3-yl]-N,N-dimethylethylamine maleate 0.95 hydrate (white lyopholate);

26) 2-{5-[2-(2,5-Dioxoimidazolidinyl)ethyl]-1H-indol-3-yl}ethylamine hydrochloride hydrate, mp 83°–85° C.;

27) 2-{5-[2-(2,5-Dioxoimidazolindinyl)ethyl]-1H-indol-3-yl}-N,N-dimethylethylamine maleate hydrate (pale yellow lyopholate);

28) 5-[2-(2,5-Dioxoimidazolidinyl)ethyl]-3-(1-methyl-4-piperidinyl)-1H-indole hydrochloride, mp 320°–322° C. (dec);

29) 2-[5-(5-Methyl-2-oxoimidazolidin-4-ylethyl)-1H-indol-3-yl]ethylamine maleate hydrate, mp 99° C. (softens 88° C.);

30) 5-[3-(4-Piperidyl)-1H-indol-5-ylmethyl]-2,4-imidazolidinedione acetate 1.4 hydrate, mp 92°–93° C. (softens 86° C.); and 31) 2-[5-(1-Methyl-2-oxo-4-imidazolidinylmethyl)-1H-indol-3-yl]ethylamine diacetate 2.75 hydrate (pale yellow lyophylate).

PHARMACEUTICAL FORMULATION EXAMPLES

In the following Examples, the "active ingredient" may be any compound of formula (I) and/or a physiologically acceptable salt, solvate, or physiologically functional derivative thereof.

(1) Tablet Formulations

| | Mg/tablet | | |
|---|---|---|---|
| (i) Oral | A | B | C |
| Active ingredient | 25 | 25 | 25 |
| Avicel | 13 | — | 7 |
| Lactose | 78 | 47 | — |
| Starch (maize) | — | 9 | — |
| Starch (pre-gelatinised, NFI5) | — | — | 32 |
| Sodium starch glycollate | 5 | — | — |
| Povidone | 3 | 3 | — |
| Magnesium stearate | 1 | 1 | 1 |
| | 125 | 85 | 65 |

| (ii) Sublingual | D | E |
|---|---|---|
| Active ingredient | 25 | 25 |
| Avicel | 10 | — |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
| | 90 | 125 |

Formulations A to E may be prepared by wet granulation of the first six ingredients with the povidone, followed by addition of the magnesium stearate and compression.

| (iii) Buccal | Mg/tablet |
|---|---|
| Active ingredient | 25 |
| Hydroxypropylmethyl cellulose (HPMC) | 25 |
| Polycarbophil | 39 |
| Magnesium stearate | 1 |
| | 90 |

The formulation may be prepared by direct compression of the admixed ingredients.

(2) Capsule formulations

| | Mg/capsule | |
|---|---|---|
| (i) Powder | F | G |
| Active ingredient | 25 | 25 |
| Avicel | 45 | — |
| Lactose | 153 | — |
| Starch (1500 NF) | — | 117 |
| Sodium starch glycollate | — | 6 |
| Magnesium stearate | 2 | 2 |
| | 225 | 150 |

Formulations F and G may be prepared by admixing the ingredients and filling two-part hard gelatin capsules with the resulting mixture.

| | Mg/capsule | |
|---|---|---|
| (ii) Liquid fill | H | I |
| Active ingredient | 25 | 25 |
| Macrogol 4000 BP | 200 | — |
| Lecithin | — | 100 |
| Arachis oil | — | 100 |
| | 225 | 225 |

Formulation H may be prepared by melting the Macrogol 4000 BP. dispersing the active ingredient in the melt and filling two-part hard gelatin capsules therewith. Formulation I may be prepared by dispersing the active ingredient in the lecithin and arachis oil and filling soft, elastic gelatin capsules with the dispersion.

| (iii) Controlled release | Mg/capsule |
|---|---|
| Active ingredient | 25 |
| Avicel | 123 |
| Lactose | 62 |

| (iii) Controlled release | Mg/capsule |
|---|---|
| Triethylcitrate | 3 |
| Ethyl cellulose | 12 |
| | 225 |

The formulation may be prepared by mixing and extruding the first four ingredients and spheronising and drying the extrudate. The dried pellets are coated with ethyl cellulose as a release controlling membrane and filled into two-part, hard gelatin capsules.

(3) Intravenous injection formulation

| | % by weight |
|---|---|
| Active ingredient | 2% |
| Hydrochloric acid } | q.s. to pH 7 |
| Citrate buffer | |
| Water for Injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are sealed and oversealed.

(4) Intranasal formulation

| | % by weight |
|---|---|
| Active ingredient | 0.5% |
| Hydrochloric acid } | q.s. to pH 7 |
| Citrate buffer | |
| Methyl hydroxybenzoate | 0.2% |
| Propyl hydroxybenzoate | 0.02 |
| Water for Injections | to 100% |

The active ingredient is taken up in a mixture of the hydroxybenzoates and citrate buffer and sufficient hydrochloric acid added to affect solution and adjust the pH to 7. The resulting solution is made up to volume and filtered through a micropore filter into sterile glass vials which are sealed and oversealed.

(5) Intramuscular injection formulation

| Active ingredient | 0.05 g |
|---|---|
| Benzyl alcohol | 0.10 g |
| Glycofurol 75 | 1.45 g |
| Water for Injections q.s. to | 3.00 ml |

The active ingredient is dissolved in the glycofurol. The benzyl alcohol is added and dissolved and water added to 3 ml. The mixture is filtered through a micropore filter into sterile glass vials which are sealed and oversealed.

(6) Syrup formulation

| Active ingredient | 0.05 g |
|---|---|
| Sorbitol solution | 1.50 g |
| Glycerol | 1.00 g |
| Sodium benzoate | 0.005 g |
| Flavour | 0.0125 ml |

The sodium benzoate is dissolved in a portion of the purified water and the sorbitol solution added. The active ingredient is added and dissolved. The resulting solution is mixed with the glycerol and made up to the required volume with purified water.

(7) Suppository Formulation

| | Mg/suppository |
|---|---|
| Active ingredient (63 μm)* | 50 |
| Hard fat, BP (Witepsol H15 - Dynamit NoBel) | 1950 |
| | 2000 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and mixed with the molten base using a Silverson mixer fitted with a cutting head until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°–40° C., 2.0 g aliquots of the mixture are filled into suitable plastic moulds and the suppositories allowed to cool to room temperature.

(8) Pessary Formulation

| | Mg/pessary |
|---|---|
| Active ingredient (63 μm) | 50 |
| Anhydrous dextrose | 470 |
| Potato starch | 473 |
| Magnesium stearate | 473 |
| | 1000 |

The above ingredients are mixed directly and pessaries prepared by compression of the resulting mixture.

BIOLOGICAL ASSAY

The compounds of formula (I) prepared in Synthetic Examples 1 to 17 were each tested for their activity as agonists for the "5-HT$_1$-like" receptor mediating smooth muscle contraction by the following method.

Right and left lateral saphenous veins were obtained from male New Zealand White rabbits (2.4–2.7 kg) which had been killed by intravenous injection of pentobarbitone sodium (60 mg/kg). Ring segments (3–5 mm wide) prepared from each vessel were suspended between two wire hooks and immeresed in 20 ml organ baths containing Krebs' solution (pH 7.4) of the following composition (mM): NaCl 118.41, NaHCO$_3$ 25.00, KCl 4.75, KH$_2$PO$_4$ 1.19, MgSO$_4$ 1.19, glucose 11.10 and CaCl$_2$ 2.50. Cocaine (30 μM) was present in the Krebs' solution throughout the experiment to prevent the uptake of amines by sympathetic neurones. The Krebs' solution was maintained at 37° C. and continually gassed with 95% oxygen/5% carbon dioxide. Increases in tissue isometric force were measured using Grass FT03C force displacement transducers and recorded on a Gould BD-212 pen recorder.

A force of 1.0 g was applied to each preparation and re-established twice during a subsequent period of 30 minutes. During this period, tissues were exposed to pargyline (500 μM) to irreversibly inhibit monoamine oxidase and to phenoxybenzamine (0.1 μM) to inactivate α$_1$-adrenoceptors. At the end of the 30 minutes, the inhibitors were removed by several changes of the organ bath Krebs' solution.

Agonist activity was assessed by cumulative additions of the test compound, its concentration being increased in 0.5 log$_{10}$ unit increments until further additions caused no further change in tissue force. In each experiment, the activity of the test compound was compared to the activity of 5-HT. Activity was expressed in terms of the p[A$_{50}$] ($-\log_{10}$[M]), where M is the molar concentration of agonist required to produce half the maximum effect). The results obtained for the compounds of Synthetic Examples 2/3 and 4/5 are shown in Table 1.

TABLE 1

| Example | Activity p(A$_{50}$) |
|---------|----------------------|
| 2/3     | 7.0                  |
| 4/5     | 6.3                  |

TOXICITY DATA

The hydrochloride salt of the compound of Synthetic Examples 2/3 was administered orally by gavage to Wistar rats as a solution in distilled water at dosages of 25, 100 and 200 mg/kg base and to Beagle dogs at dosages of 0.25, 0.50, 1.0 and 2.0 mg/kg base once a day for 14 days. In a separate dog study over 30 days, the dosage of the free base was increased from 2 mg/kg on Day 1 to 100 mg/kg on Day 30. The free base was also administered orally to cynomolgus monkeys at a dosage of 50 mg/kg once a day for 15 days.

No evidence of toxicity was observed in any of the aforementioned studies at any of the dosages used.

We claim:

1. A compound of the formula:

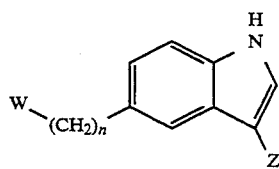

wherein
n is an integer of from 0 to 3;
W is a group of formula (i), (ii), or (iii)

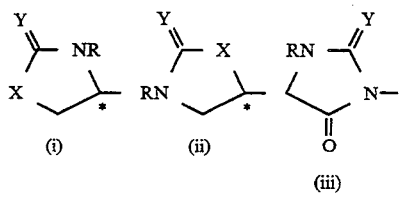

wherein R is hydrogen or C$_{1-4}$ alkyl, X is —O—, —S—, —NH—, or —CH$_2$—, Y is oxygen or sulphur and the chiral center * in formula (i) or (ii) is in its (S) or (R) form or is a mixture thereof in any proportions; and
Z is a group of the formula:

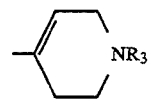

wherein R$^3$ is hydrogen or C$_{1-4}$ alkyl;
its solvate or a physiologically acceptable salt thereof.

2. A method of preventing or treating migraine comprising administering to a patient in need of same an effective amount of a compound of claim 1 or a physiologically acceptable salt or solvate thereof.

3. The method as claimed in claim 2 in which the patient is a human.

4. A pharmaceutical composition comprising an effective amount of the compound of claim 1 or a physiologically acceptable salt or solvate thereof together with a pharmaceutically acceptable carrier.

5. The pharmaceutical composition of claim 4 which is in the form of a tablet or capsule.

* * * * *